(12) United States Patent
Nishihara et al.

(10) Patent No.: US 9,921,284 B2
(45) Date of Patent: Mar. 20, 2018

(54) MAGNETIC RESONANCE IMAGING APPARATUS AND MAGNETIC RESONANCE IMAGING METHOD, CONFIGURED TO ADJUST MULTI-DIMENSIONAL SELECTIVE EXCITATION PULSE

(71) Applicant: HITACHI, LTD., Tokyo (JP)

(72) Inventors: Takashi Nishihara, Tokyo (JP); Hiroyuki Itagaki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 511 days.

(21) Appl. No.: 14/418,246

(22) PCT Filed: Sep. 10, 2013

(86) PCT No.: PCT/JP2013/074353
§ 371 (c)(1),
(2) Date: Jan. 29, 2015

(87) PCT Pub. No.: WO2014/045936
PCT Pub. Date: Mar. 27, 2014

(65) Prior Publication Data
US 2015/0260815 A1 Sep. 17, 2015

(30) Foreign Application Priority Data
Sep. 20, 2012 (JP) ................................. 2012-207081

(51) Int. Cl.
*G01V 3/00* (2006.01)
*G01R 33/483* (2006.01)
(Continued)

(52) U.S. Cl.
CPC .......... *G01R 33/4836* (2013.01); *A61B 5/055* (2013.01); *G01R 33/36* (2013.01);
(Continued)

(58) Field of Classification Search
CPC .. G01R 33/4836; G01R 33/36; G01R 33/385; G01R 33/543; G01R 33/561; G01R 33/546; A61B 5/055
(Continued)

(56) References Cited

U.S. PATENT DOCUMENTS

| 2012/0176132 A1* | 7/2012 | Nishihara | A61B 5/055 324/309 |
| 2012/0194190 A1 | 8/2012 | Goto et al. | |
| 2013/0265053 A1* | 10/2013 | Itagaki | G01R 33/543 324/309 |

FOREIGN PATENT DOCUMENTS

| JP | 5-200012 | 8/1993 |
| JP | 2001-95773 | 4/2001 |

(Continued)

OTHER PUBLICATIONS

International Search Report in PCT/JP2013/074353, dated Oct. 2013.
(Continued)

*Primary Examiner* — Susan Lee
(74) *Attorney, Agent, or Firm* — Cooper & Dunham LLP

(57) ABSTRACT

In order to provide a technique for improving image quality by selectively exciting only a target region with high precision in either of a two-dimensional spatial selective excitation method or a three-dimensional spatial selective excitation method, selecting a k-space trajectory restraining excitation in a non-target region by side lobes is received. At this time, an excitation region of the selected k-space trajectory is presented to an operator, and the operator can adjust the excitation region through the display. After the adjustment of the excitation region by the operator is reflected, a multi-dimensional spatial selective excitation pulse is stabilized.

15 Claims, 18 Drawing Sheets

(51) Int. Cl.
  *A61B 5/055* (2006.01)
  *G01R 33/36* (2006.01)
  *G01R 33/385* (2006.01)
  *G01R 33/54* (2006.01)
  *G01R 33/561* (2006.01)

(52) U.S. Cl.
  CPC ......... *G01R 33/385* (2013.01); *G01R 33/543* (2013.01); *G01R 33/561* (2013.01); *G01R 33/546* (2013.01)

(58) Field of Classification Search
  USPC .......................................................... 324/309
  See application file for complete search history.

(56) References Cited

FOREIGN PATENT DOCUMENTS

| | | |
|---|---|---|
| JP | 2002-233515 | 8/2002 |
| JP | 2009-18079 | 1/2009 |
| JP | 2009-291388 | 12/2009 |
| WO | WO 2001/022879 | 4/2001 |
| WO | WO 2011/040289 | 4/2011 |

OTHER PUBLICATIONS

Glenn Morrell, "Three-Dimensional Spectral-Spatial Excitation", Magnetic Resonance in Medicine, 1997, vol. 37, p. 378-386.

* cited by examiner

FIG.1
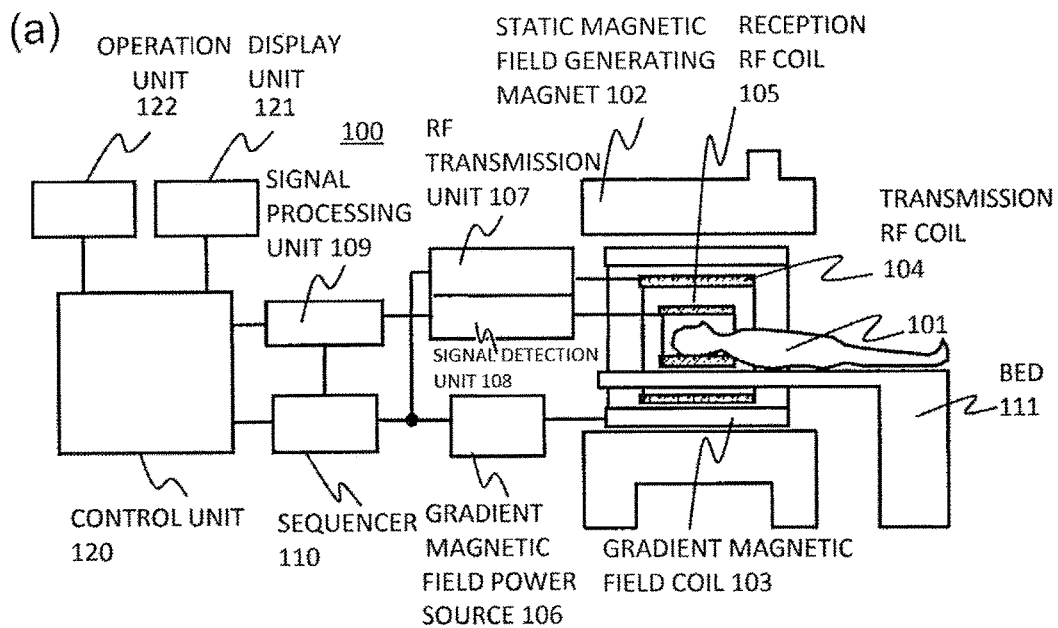
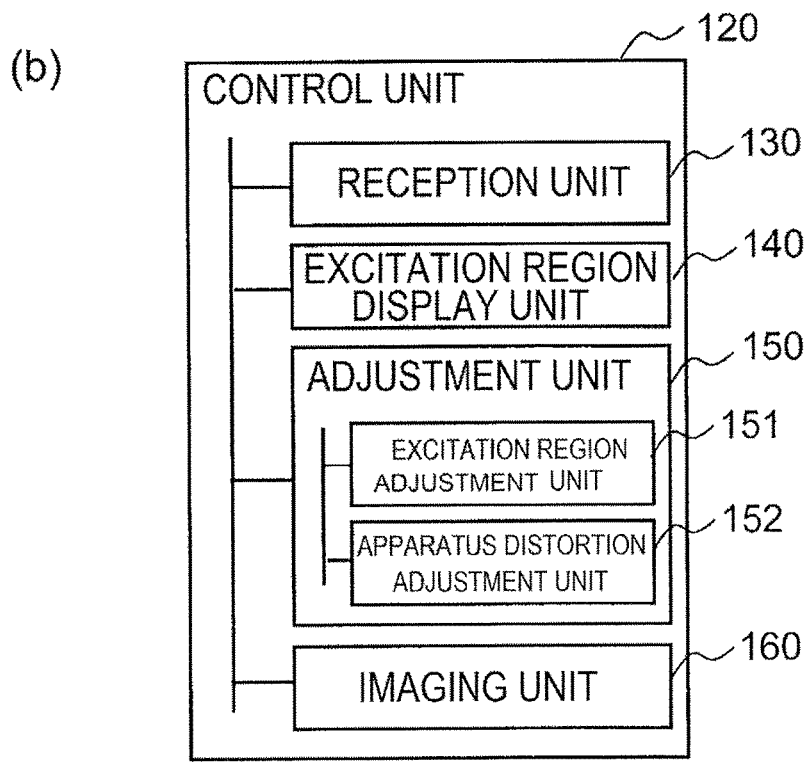

FIG.3
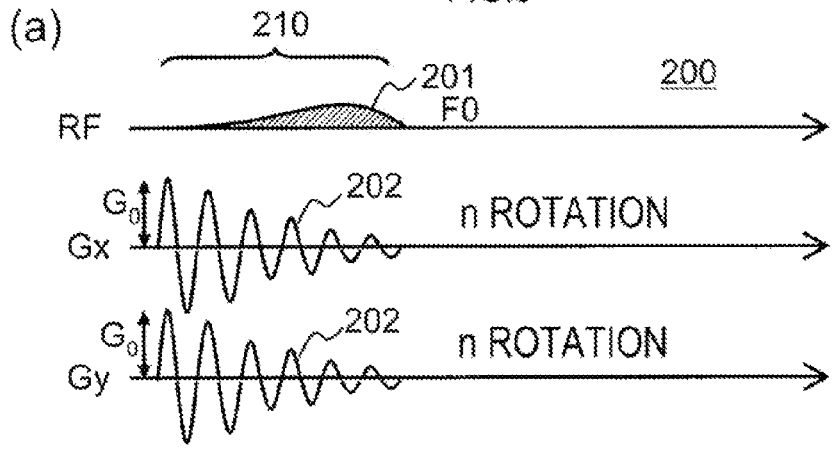
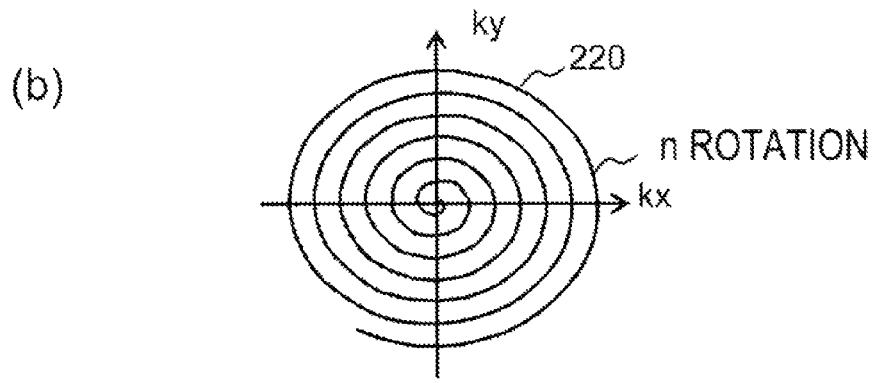
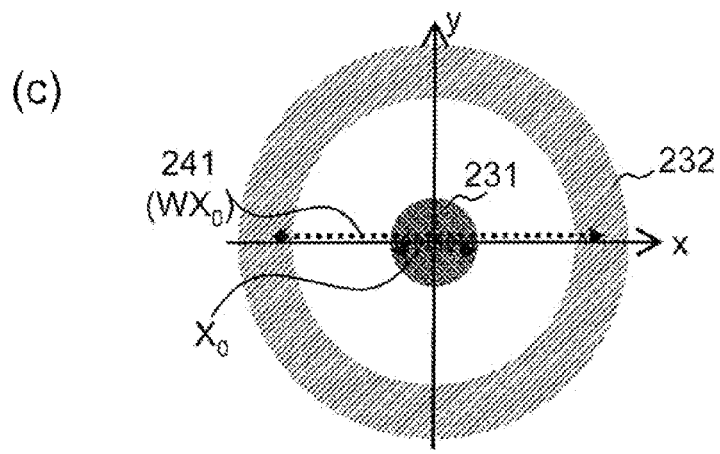
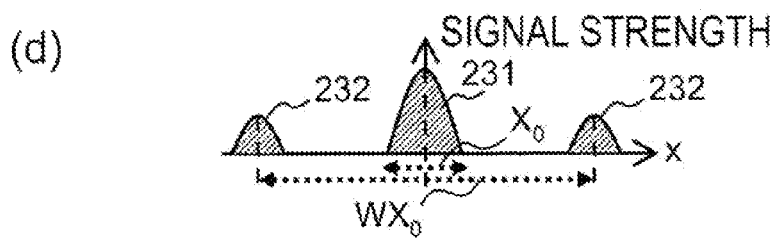

FIG.4
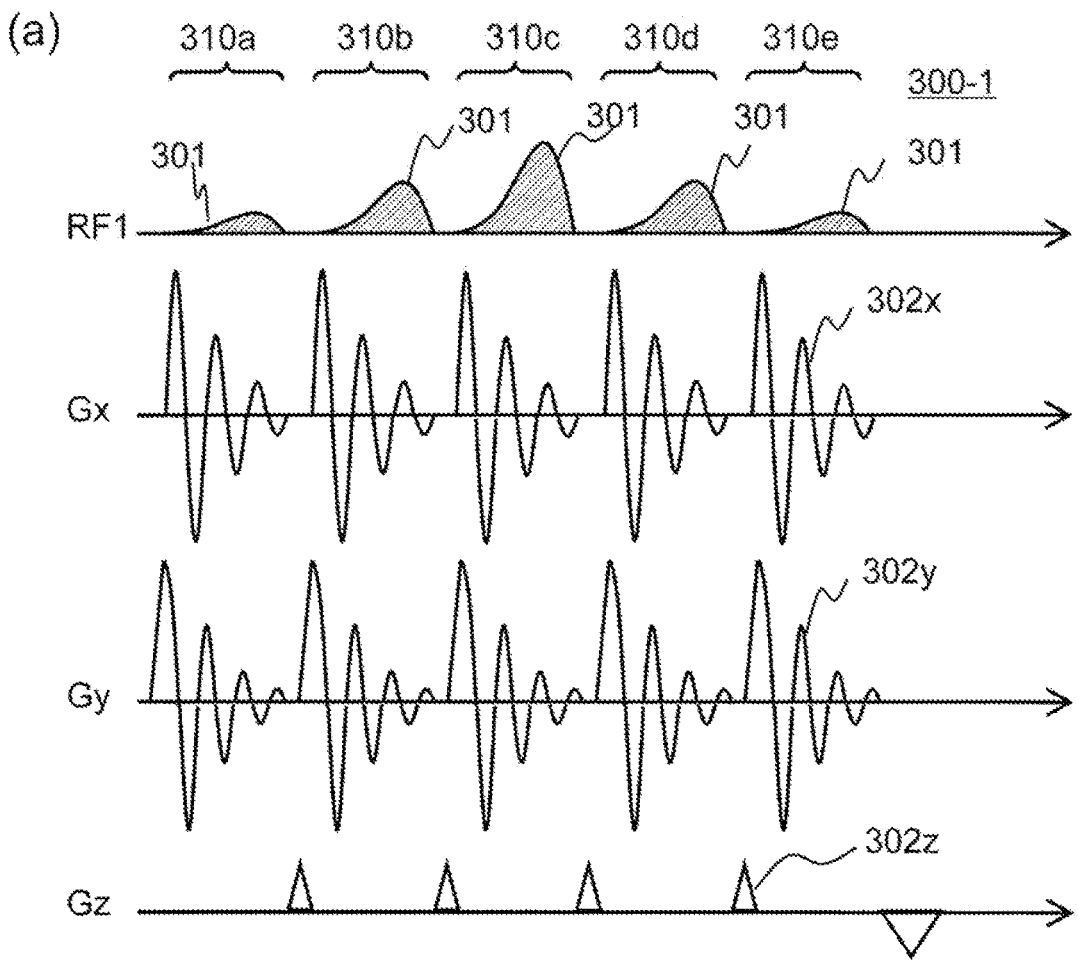
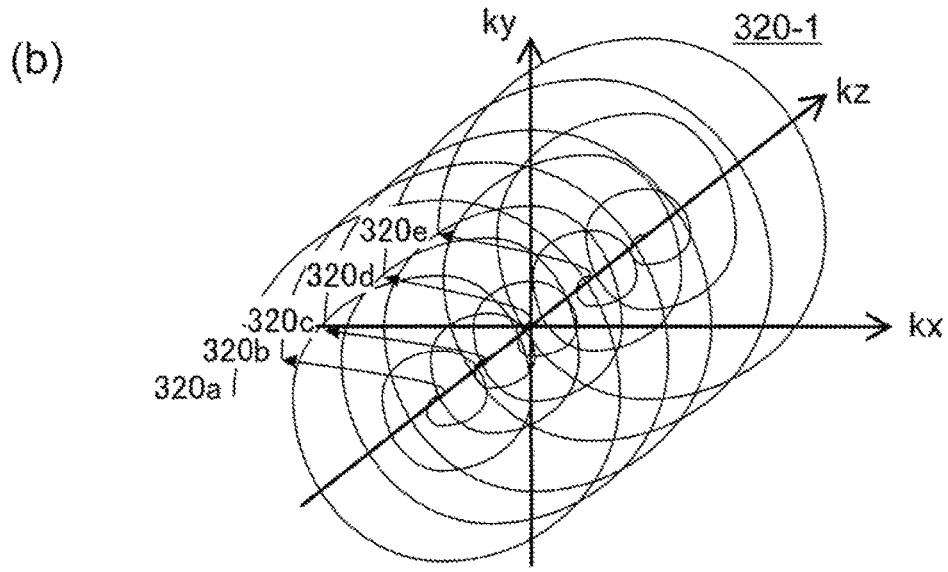

FIG.5
(a)
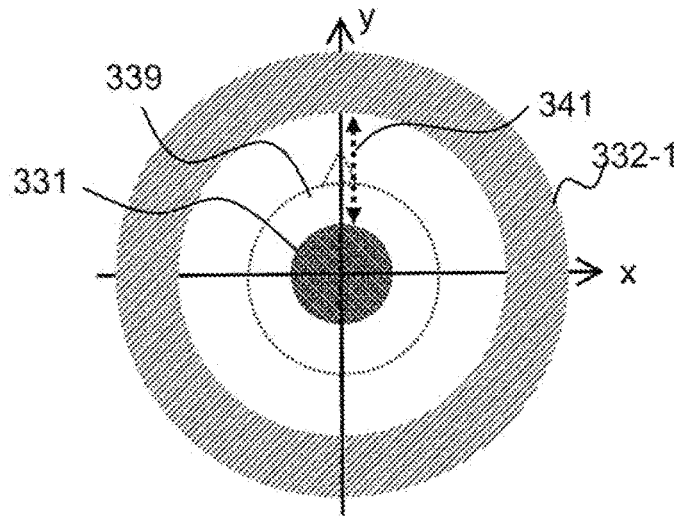
(b)
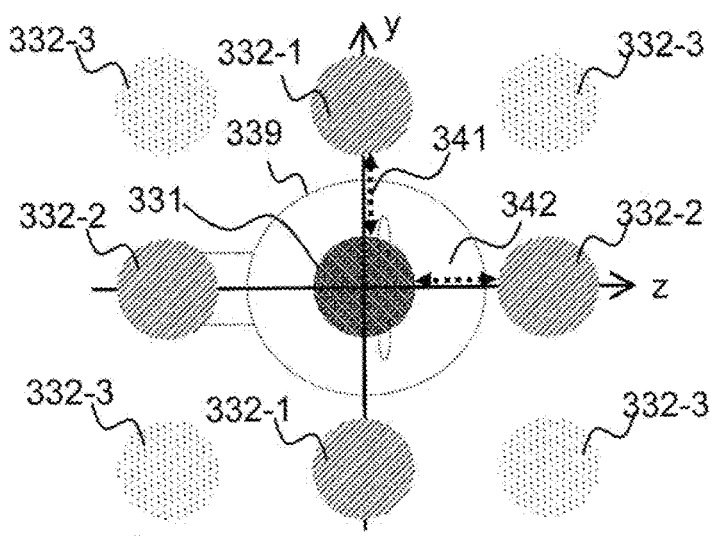
(c)
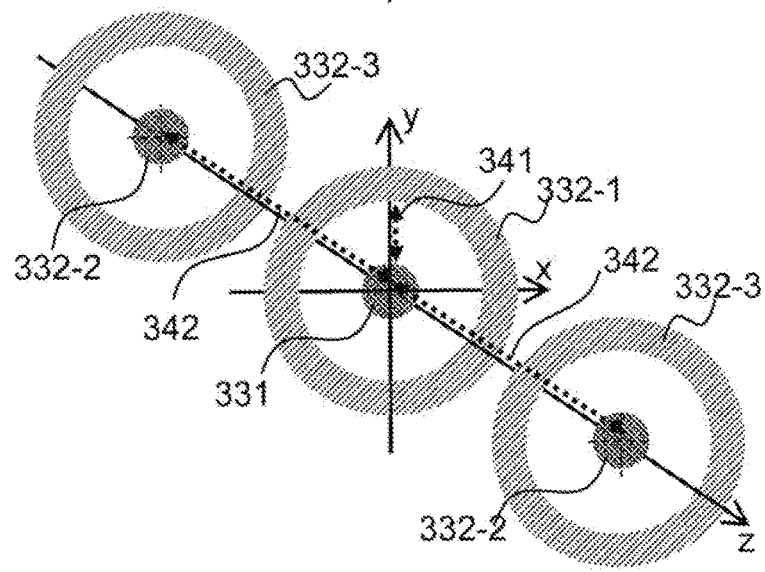

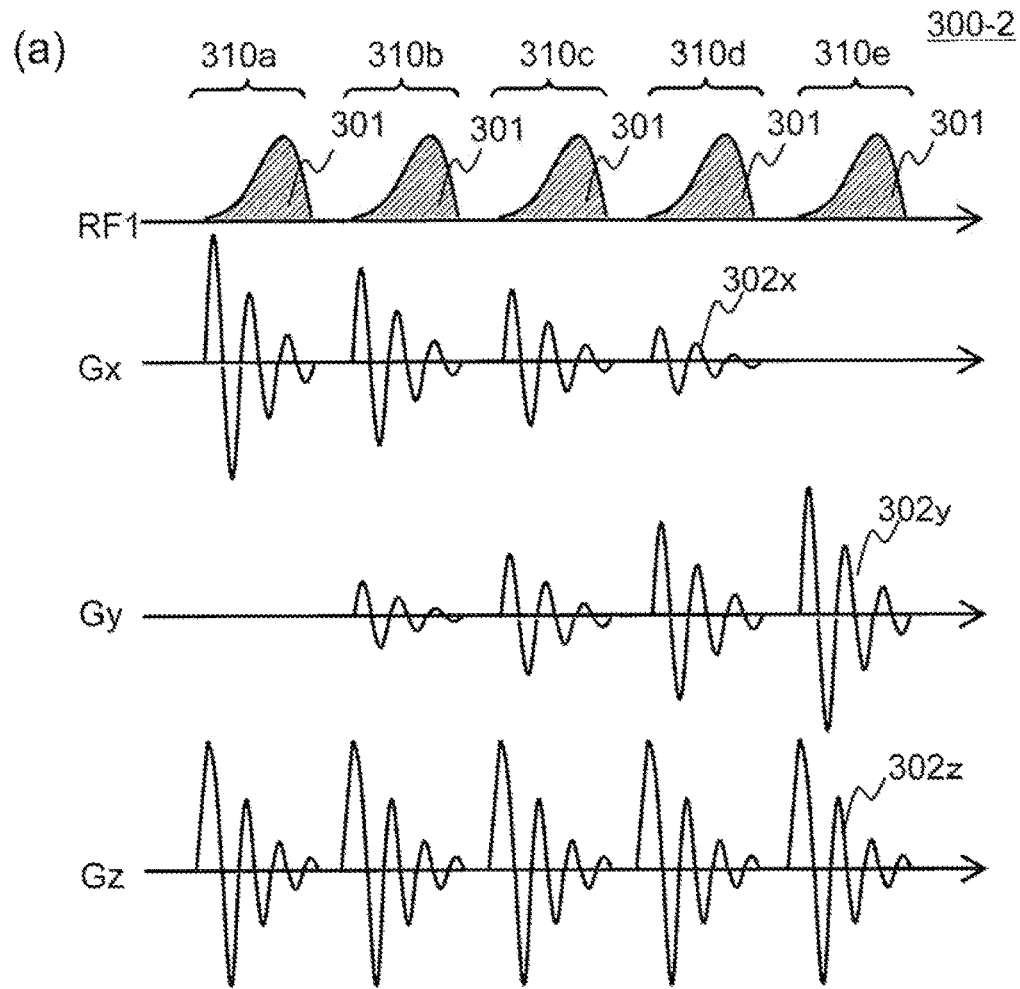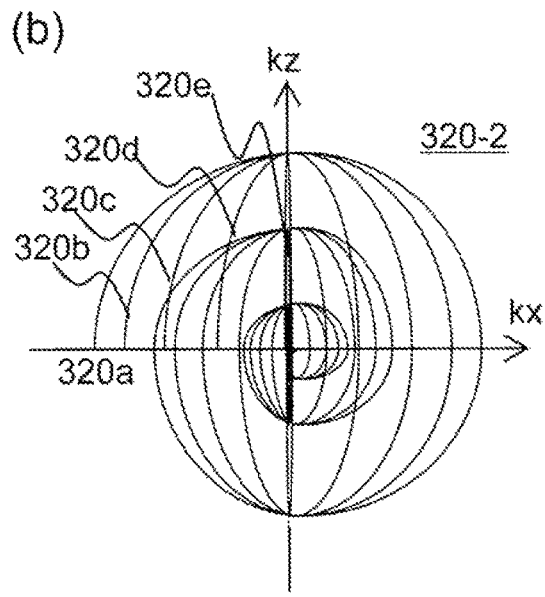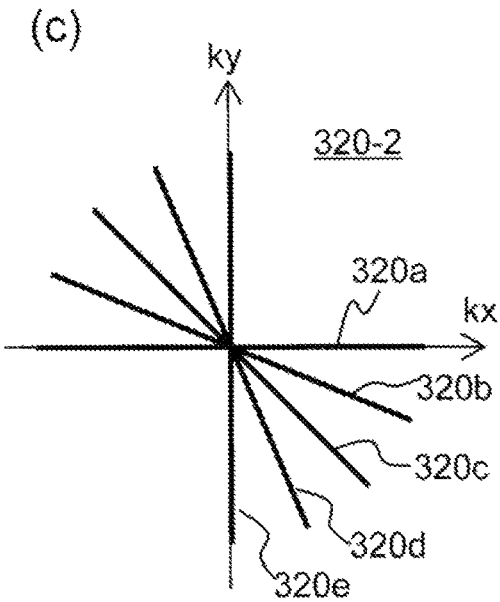
FIG.6

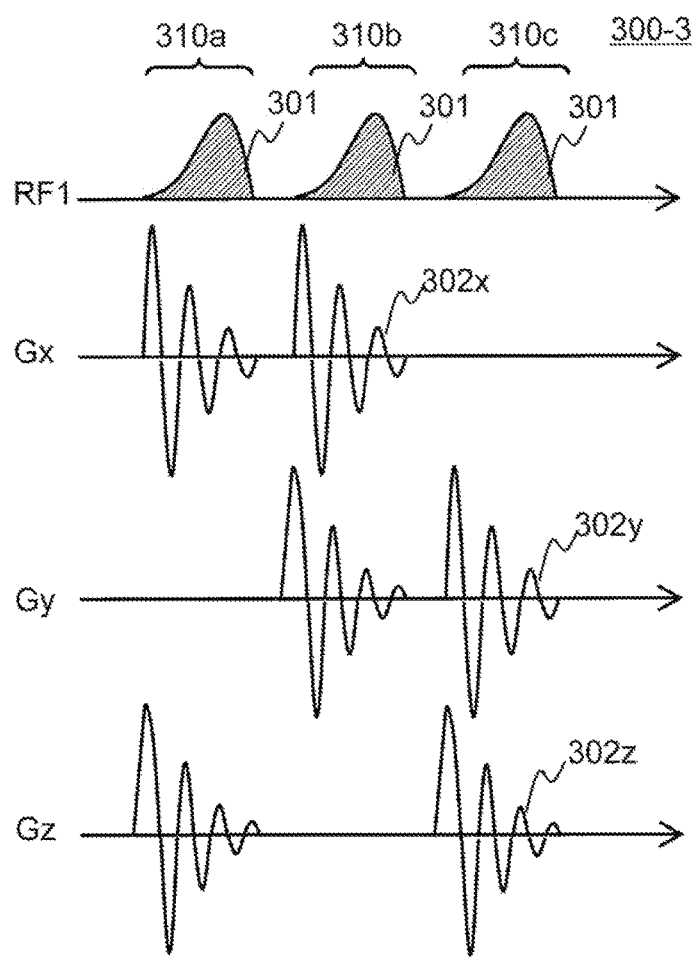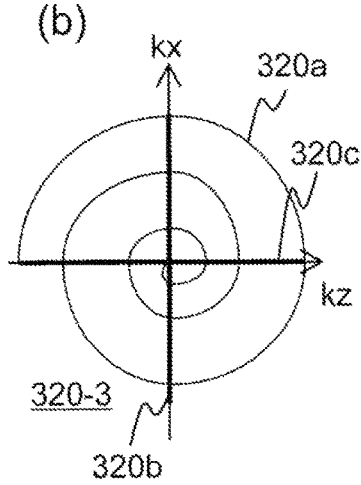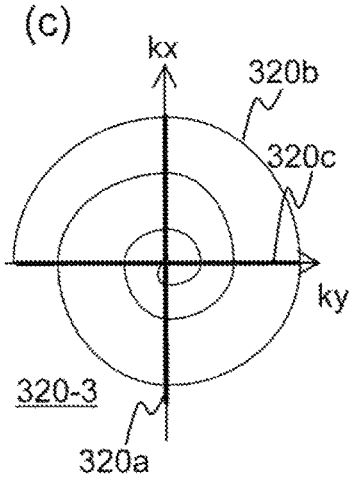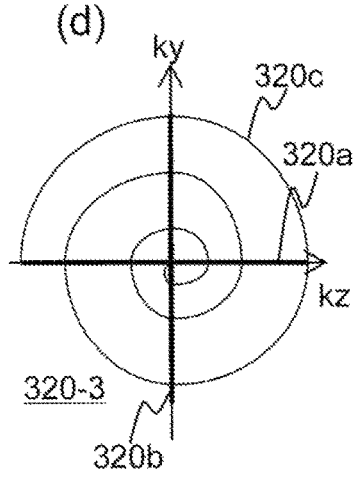
FIG.8

FIG. 9
(a) 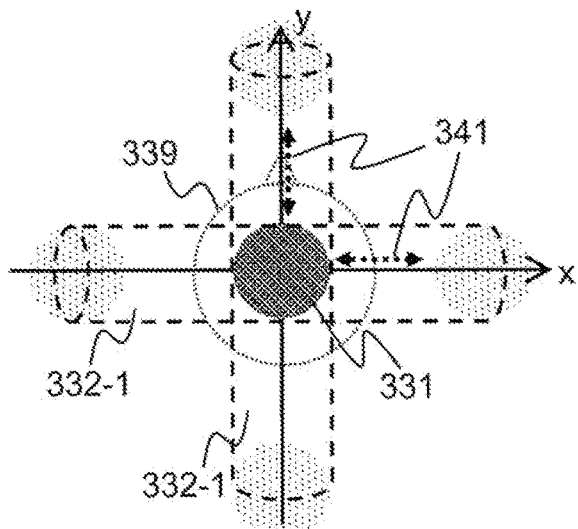
(b) 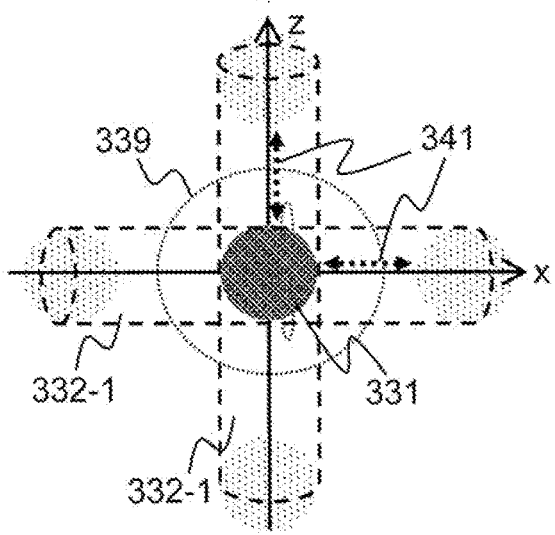
(c) 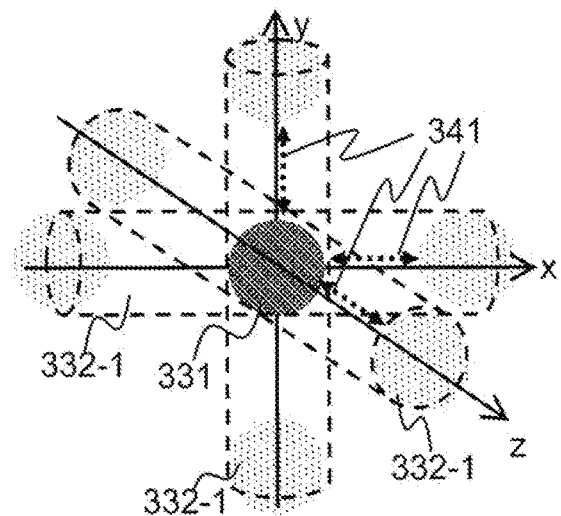

FIG.10
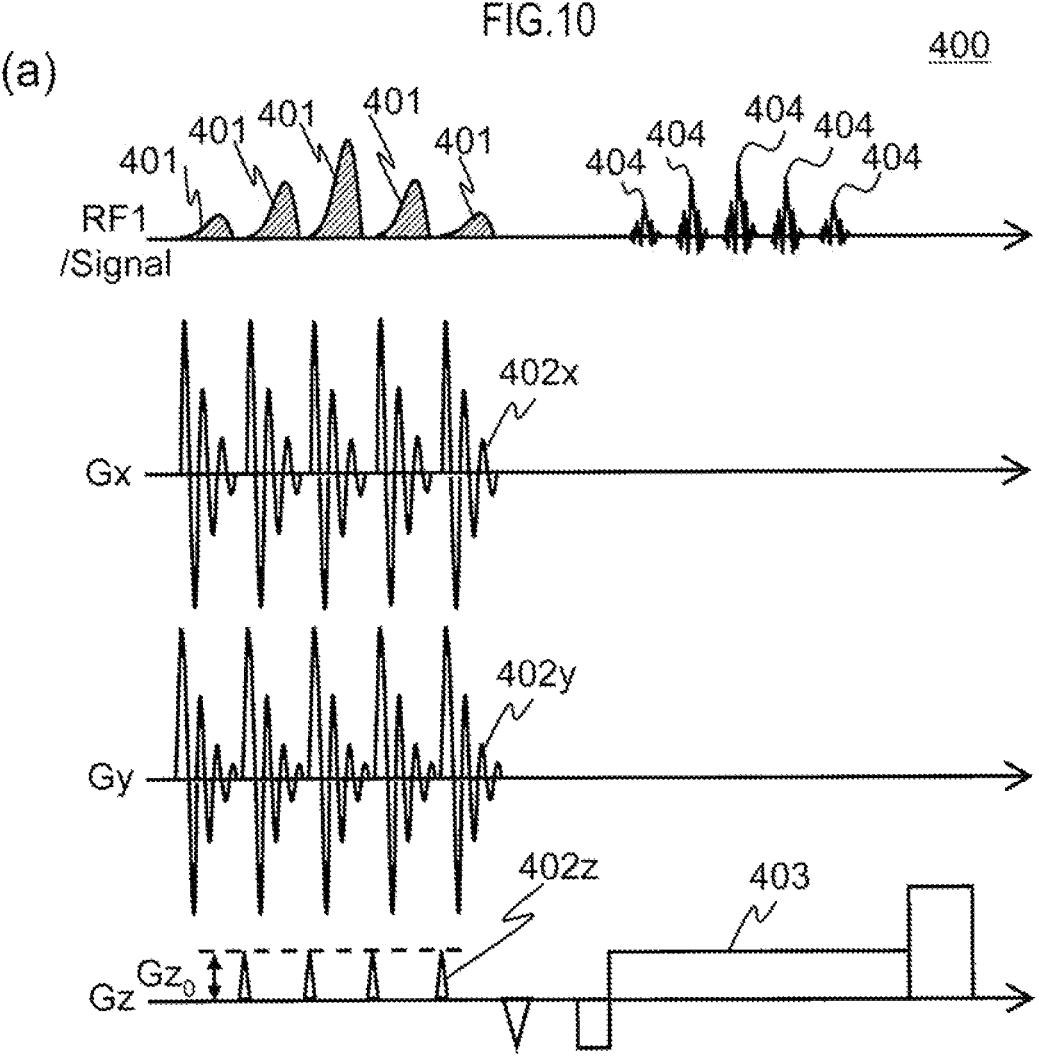
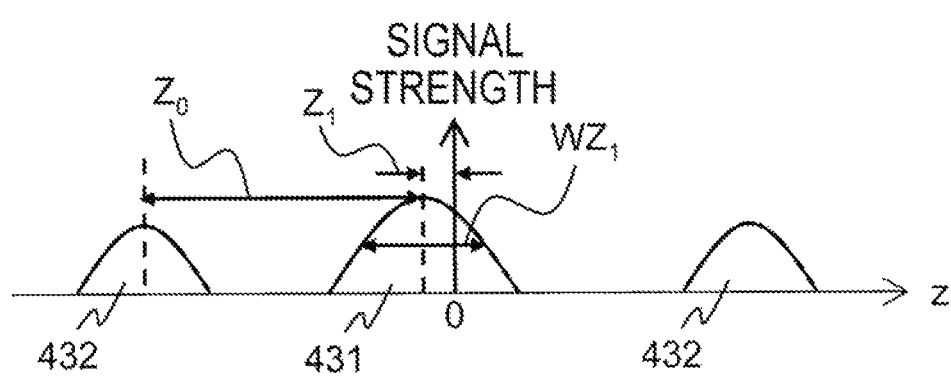

FIG.14
(a)
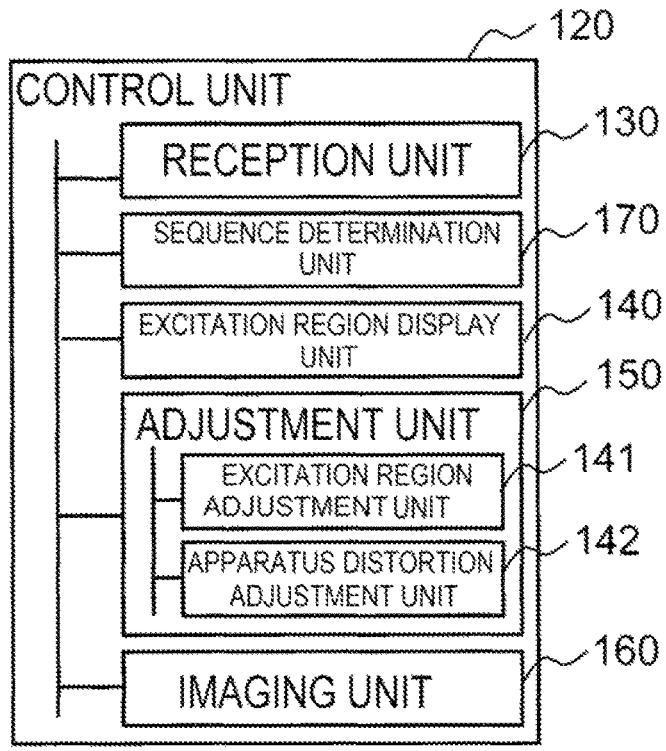
(b)
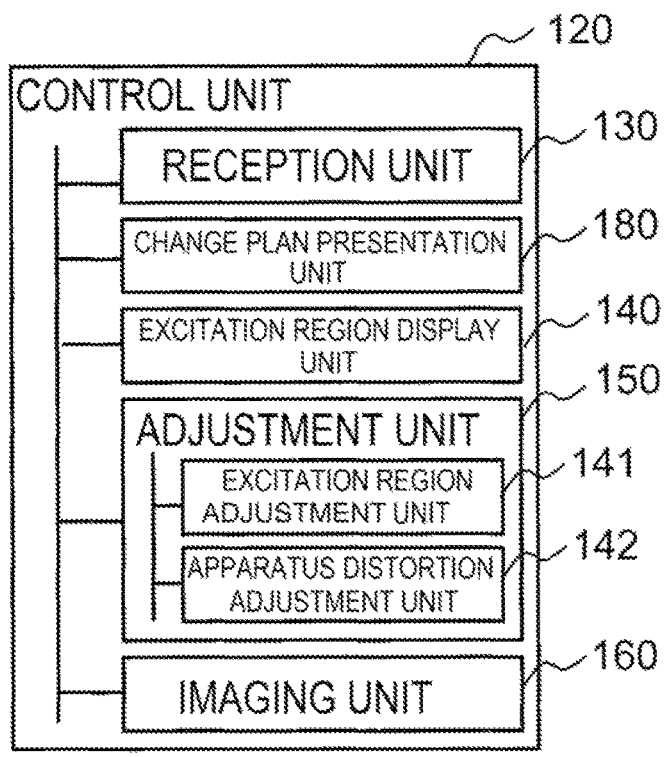

FIG.15
(a)
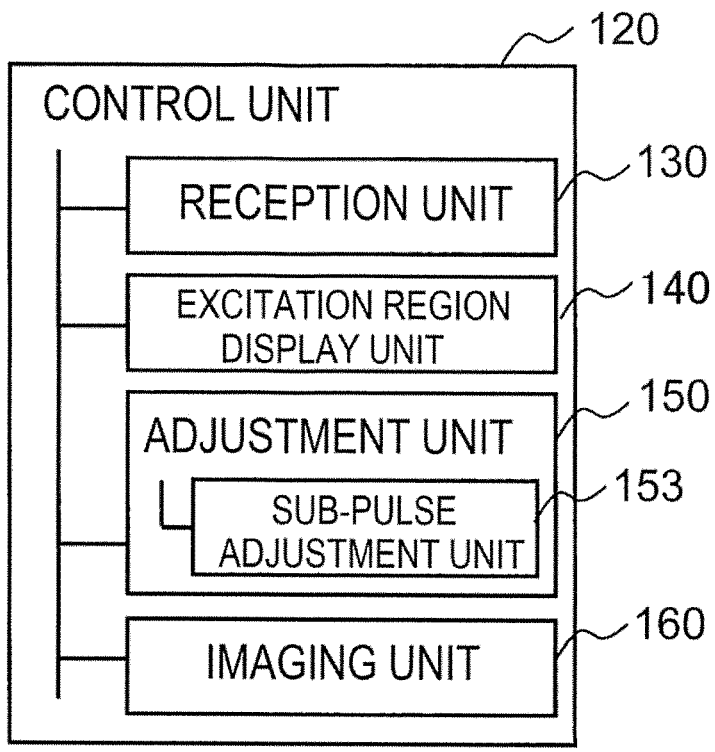
(b)
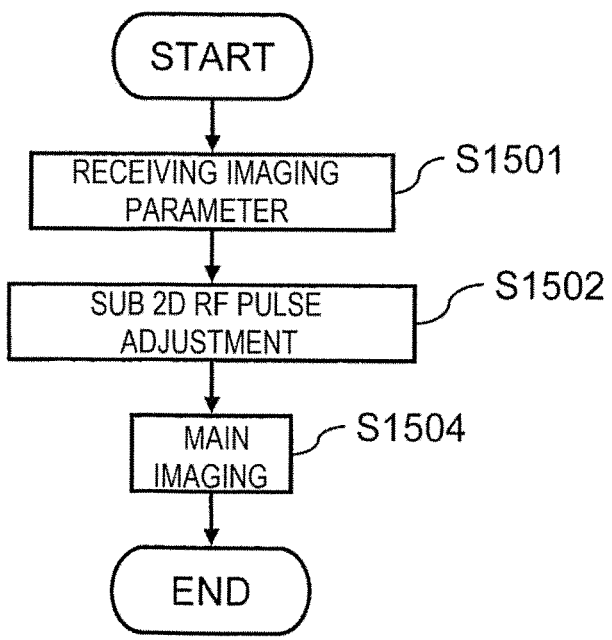

FIG.16
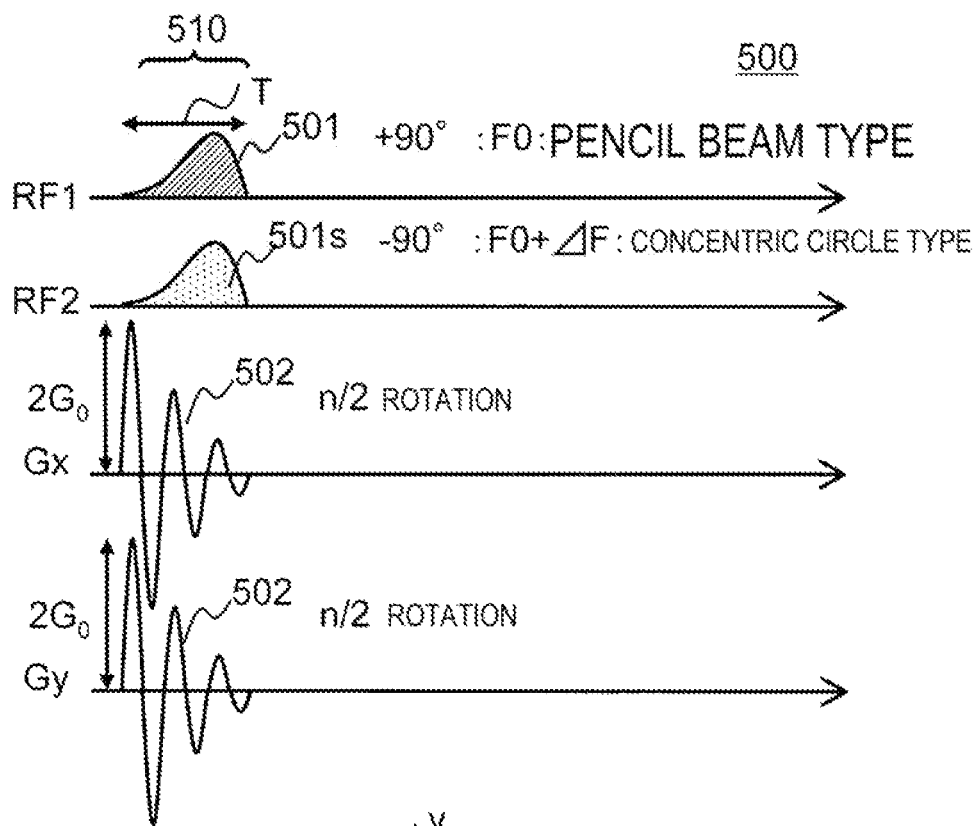
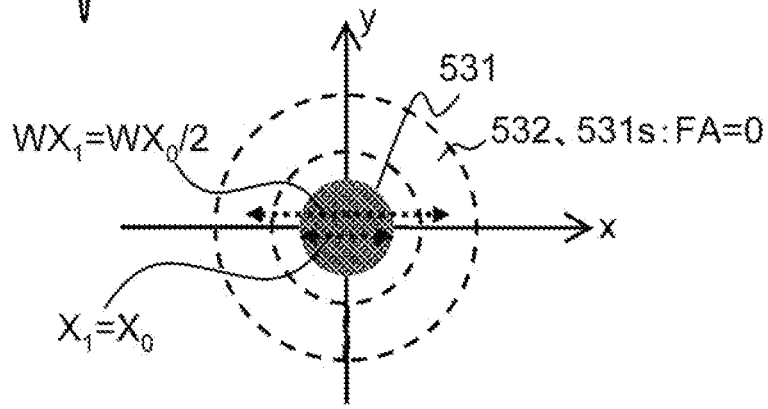
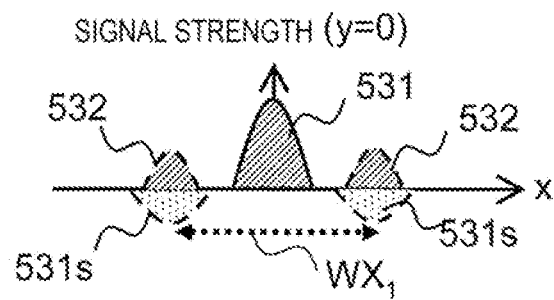

FIG.18
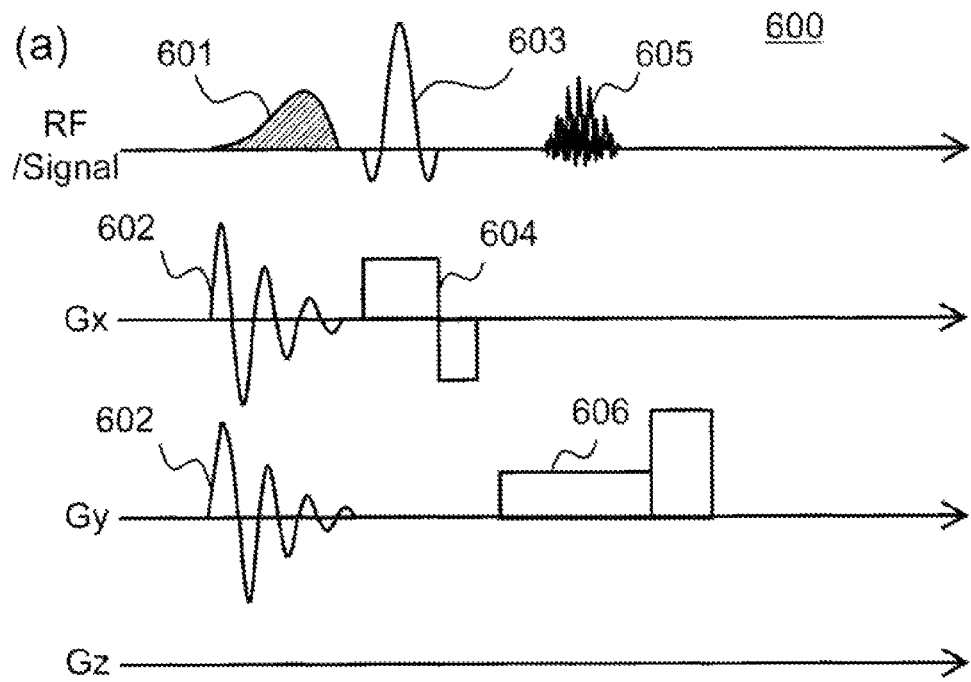
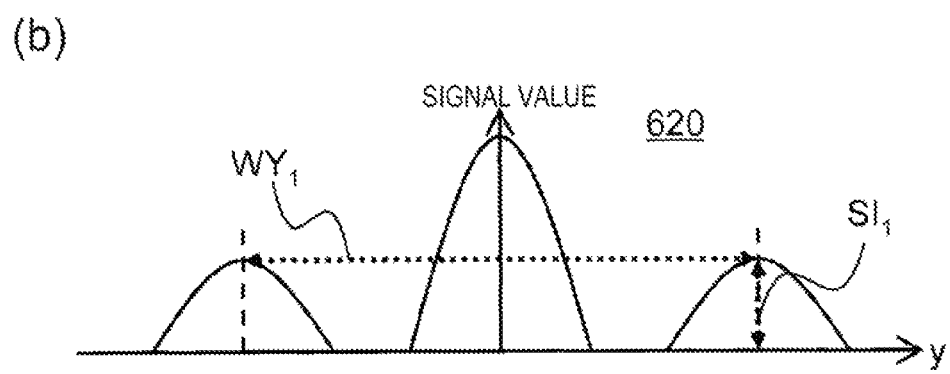
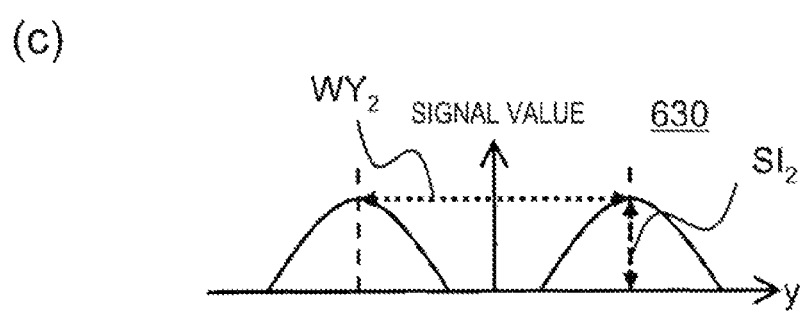

MAGNETIC RESONANCE IMAGING APPARATUS AND MAGNETIC RESONANCE IMAGING METHOD, CONFIGURED TO ADJUST MULTI-DIMENSIONAL SELECTIVE EXCITATION PULSE

TECHNICAL FIELD

The present invention relates to the Magnetic Resonance Imaging (hereinafter, referred to as MRI) technique, in particular to an imaging technique by a sequence in which a spatial selective excitation pulse is used.

BACKGROUND ART

Normally, MRI uses a radio wave (hereinafter, RF) and a gradient magnetic field to selectively excite an arbitrary plane with a thickness in a one-dimensional direction. Also, there is a two-dimensional spatial selective excitation (spectral-spatial; hereinafter, referred to as SS) method of identifying two directions and selectively exciting only the inside of a region limited by the two directions. In the two-dimensional spatial selective excitation method, an RF pulse is applied in addition to an oscillating gradient magnetic field pulse. At this time, the RF pulse applied in addition to the oscillating gradient magnetic field pulse is referred to as a two-dimensional selective excitation pulse (2D RF pulse). Also, a pair of the 2D RF pulse and the oscillating gradient magnetic field pulse is referred to as a two-dimensional spatial selective excitation pulse.

On the contrary to this, there is a method of selectively exciting a three-dimensional space by applying a two-dimensional spatial selective excitation pulse multiple times (for example, see Non-Patent Literature 1). This method is referred to as a three-dimensional spatial selective excitation method, a plurality of RF pulses applied at this time are referred to as 3D RF pulses, and pairs of the respective 3D RF pulses and the oscillating gradient magnetic field pulse are referred to as three-dimensional spatial selective excitation pulses. Additionally, hereinafter, these pulses are referred to as a multi-dimensional spatial selective excitation pulse in the present description in a case where there is no need to distinguish between two and three dimensions in particular or a case where the two and three dimensions are included.

In the two-dimensional spatial selective excitation method, an application time of the two-dimensional selective excitation pulse is long; an excitation profile is distorted by various factors, which results in shifting an excitation position easily. The representative factors affecting an excitation profile and an excitation position are a residual magnetic field and an eddy current due to an oscillating gradient magnetic field pulse, an inhomogeneous static magnetic field, timing delay between applications of an oscillating gradient magnetic field pulse and an RF pulse (hereinafter, referred to as "GC Delay"), etc., and an excitation position shift due to these factors is referred to as an excitation position shift due to apparatus distortion in the present description. Also, reducing the excitation position shift due to apparatus distortion is referred to as pulse stabilization.

As the pulse stabilization method, there is a method in which an influence due to a residual magnetic field and an eddy current is corrected using a phase of an excitation profile (for example, see Patent Literature 1). Also, there is a technique for measuring static magnetic field inhomogeneity in a region of interest and correcting the influence (for example, see Patent Literature 2). Additionally, there is a technique for reducing timing delay between applications of an oscillating gradient magnetic field pulse and an RF pulse while changing a coefficient to determine a cylinder diameter in an excitation region and a time difference to determine an offset position (for example, see Patent Literature 3).

CITATION LIST

Patent Literature

PTL 1: WO 2011/37064
PTL 2: Japanese Patent Application Publication No. 2009-18079
PTL 3: WO 2011/040289

Non-Patent Literature

NPTL 1: Glen Morrell, Albert Macovski, "Three-Dimensional Spectral-Spatial Excitation" Magn. Reson. Med., 1997 37, p 378-386
NPTL 2: Nigel P. Davies, Peter Jezzard, Selective Arterial Spin Labeling (SASL): Perfusion Territory Mapping of Selected Feeding Arteries Tagged Using Two-Dimensional Radiofrequency Pulses, Magn. Reson. Med., 2003; 49, p 1133-1142
NPTL 3: Ulrich Katscher, Peter Bornert, Christoph Leussler, Johan S. van den Brink, Transmit SENSE, Magn. Reson. Med., 2003; 49, p 144-150

SUMMARY OF INVENTION

Technical Problem

In a sequence where a multi-dimensional spatial selective excitation pulse is used, an excitation region in a non-target region (hereinafter, referred to as "side lobe") in addition to the target excitation region (hereinafter, referred to as "main lobe") appears. Due to the side lobe, a signal comes in from a non-target region and causes artifacts. In order to improve image quality by removing the artifacts, a region where a side lobe is generated needs to be adjusted to a position where there is no influence on examinations.

However, currently, it is hard for users to understand a positional relationship between FOV and a main lobe as well as a side lobe generated according to an imaging sequence, which results in difficult adjustment. Particularly, in a three-dimensional spatial selective excitation method where a three-dimensional spatial selective excitation pulse is applied multiple times, various k-space trajectories are obtained according to how applications of the three-dimensional spatial selective excitation pulse are repeated (application pattern), and how the side lobe appears varies according to a k-space trajectory. Therefore, the adjustment is more difficult.

Also, due to the above apparatus distortion, excitation positions of a main lobe and a side lobe are changed. This results in a factor of artifacts. For a two-dimensional spatial selective excitation method, as disclosed in the above respective patent literatures, there is a pulse stabilization method reducing influences by apparatus distortion. However, an excitation profile distortion and an excitation position shift due to the apparatus distortion vary depending on a k-space trajectory. Therefore, even if a stabilization method for a 2D RF pulse is applied to a three-dimensional spatial selective excitation method to measure along various k-space trajectories as it is, pulses cannot be stabilized adequately.

Thus, in a two-dimensional spatial selective excitation method and three-dimensional spatial selective excitation method, it is difficult to selectively excite only a target region precisely. Therefore, there is a signal mixed from a non-target region, which results in artifacts deteriorating image quality.

The present invention is made in light of the above cases, and the purpose is to provide a technique for improving image quality by selectively exciting only a target region with high precision without burdening users in either of a two-dimensional spatial selective excitation method or a three-dimensional spatial selective excitation method.

Solution to Problem

The present invention accepts selection of a k-space trajectory restraining excitation in a non-target region due to a side lobe. At this time, an excitation region of the selected k-space trajectory is presented to an operator, and the operator can adjust the excitation region through the presentation. After the adjustment of the excitation region by the operator is reflected, a multi-dimensional spatial selective excitation pulse is stabilized. In order to stabilize the multi-dimensional spatial selective excitation pulse, the operator calculates an adjustment amount from previous measurement results according to the selected k-space trajectory to reflect it to an imaging sequence.

Also, the present invention applies a sub RF pulse together with a 2D RF pulse as a two-dimensional spatial selective excitation pulse. An irradiation frequency, an irradiation start phase, and an irradiation intensity are adjusted so that the side lobe of the sub RF pulse cancels out the main lobe of the 2D RF pulse.

Advantageous Effects of Invention

According to the present invention, only a target region can be selectively excited with high precision without burdening users in either of a two-dimensional spatial selective excitation method or a three-dimensional spatial selective excitation method, which results in improved image quality.

BRIEF DESCRIPTION OF DRAWINGS

FIG. 1(a) is a block diagram of the MRI apparatus 100 of the first embodiment, and FIG. 1(b) is a functional block diagram of a control unit of the first embodiment.

FIG. 3(a) is a pulse sequence to achieve two-dimensional spatial selective excitation, FIG. 3(b) is an explanatory diagram to describe the k-space trajectory, FIG. 3(c) is that for the excitation region, and FIG. 3(d) is that for the excitation profile respectively.

FIG. 4(a) is a pulse sequence to achieve three-dimensional spatial selective excitation of the first embodiment, and FIG. 4(b) is an explanatory diagram to describe the k-space trajectory.

FIGS. 5(a) to (c) are explanatory diagrams to describe a display example of an excitation region by the pulse sequence of FIG. 4(a).

FIG. 6(a) is a pulse sequence to achieve three-dimensional spatial selective excitation of the first embodiment, and FIGS. 6(b) and (c) are explanatory diagrams to describe the k-space trajectories.

FIG. 8(a) is a pulse sequence to achieve three-dimensional spatial selective excitation of the first embodiment, and FIGS. 8(b), (c), and (d) are explanatory diagrams to describe the k-space trajectories.

FIGS. 9(a) to (c) are explanatory diagrams to describe a display example of an excitation region by the pulse sequence of FIG. 8(a).

FIG. 10(a) is a pre-scan sequence example of the first embodiment, and FIG. 10(b) is an explanatory diagram to describe an excitation profile in the z direction obtained from a signal obtained by a sequence shown in (a).

FIGS. 14(a) and (b) are functional block diagrams of a variation of a control unit in the first embodiment.

FIG. 15(a) is a functional block diagram of a control unit in the second embodiment, and FIG. 15(b) is a flow chart of an imaging process in the second embodiment.

FIG. 16(a) is a pulse sequence to achieve two-dimensional spatial selective excitation of the second embodiment, FIG. 16(b) is an explanatory diagram to describe the excitation region, and FIG. 16(c) is that for the excitation profile respectively.

FIG. 18(a) is a pre-scan sequence of the second embodiment, and FIGS. 18(b) and (c) are respectively explanatory diagrams to describe an excitation profile due to a 2D RF pulse and a sub 2D RF pulse trajectories.

DESCRIPTION OF EMBODIMENTS

First Embodiment

Figure 2:
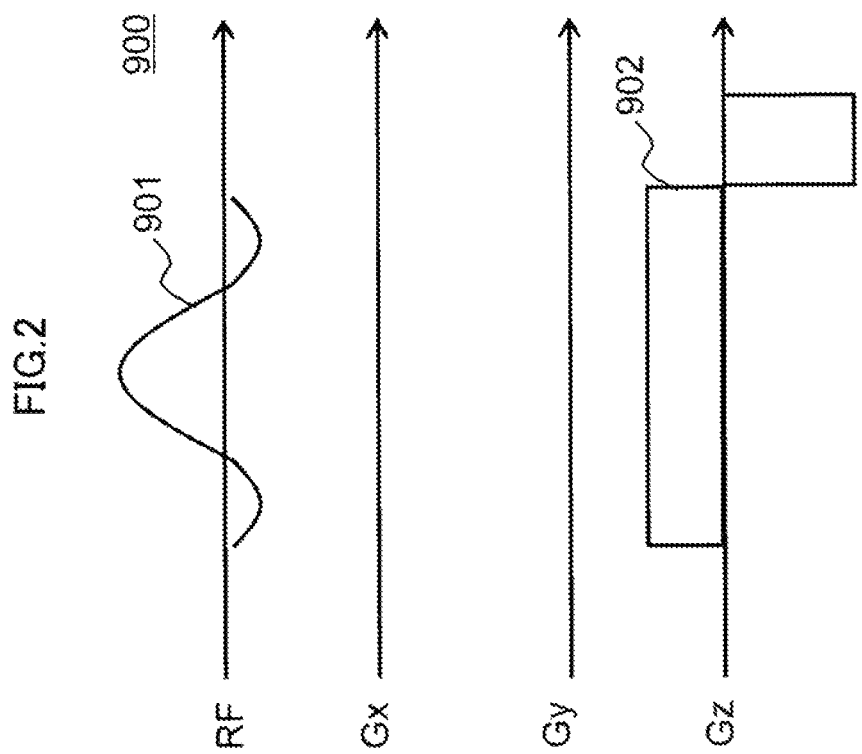
FIG. 2 is a pulse sequence by a slice selection excitation method.
Figure 7:
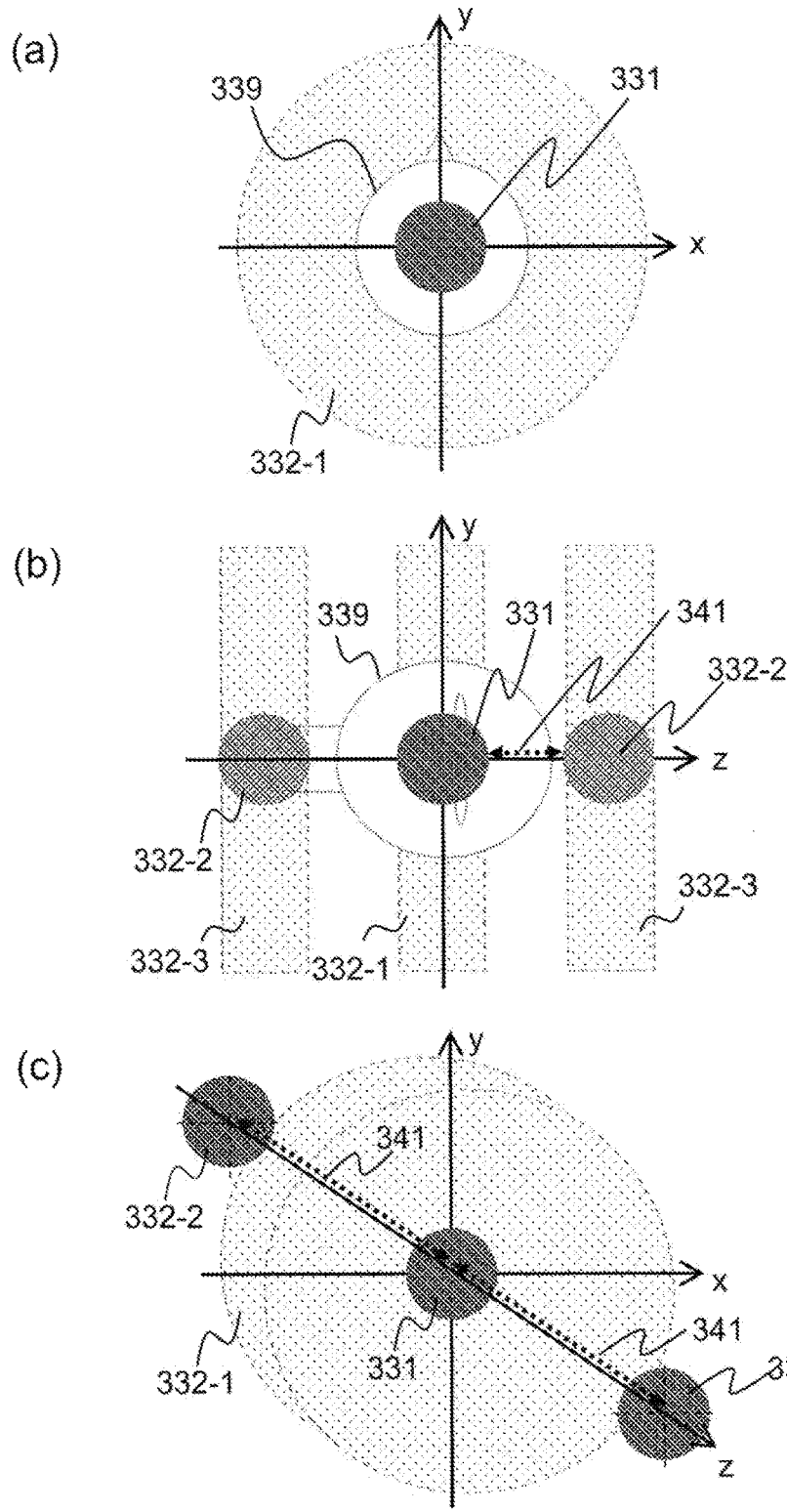
FIGS. 7(a) to (c) are explanatory diagrams to describe a display example of an excitation region by the pulse sequence of FIG. 6(a).

Hereinafter, the first embodiment applying the present embodiment will be described. Hereinafter, the same functions are denoted by the same reference numerals in all the diagrams to describe the embodiments of the present invention, and the repeated description will be omitted.

First, the MRI apparatus configuration of the present embodiment will be described. FIG. 1(a) is a block diagram of the MRI apparatus 100 of the present embodiment. The MRI apparatus 100 of the present embodiment is an apparatus obtaining a tomographic image of the object 101 using the NMR phenomenon. As shown in FIG. 1(a), the apparatus is comprised of the static magnetic field generating magnet 102, the gradient magnetic field coil 103, the gradient magnetic field power source 106, the transmission RF coil (transmission coil) 104, the RF transmission unit 107, the reception RF coil (reception coil) 105, the signal detection unit 108, the signal processing unit 109, the sequencer 110, the control unit 120, the display unit 121, the operation unit 122, and the bed 111 placing the object 101 and carry the object 101 in and out of the inside of the static magnetic field generating magnet 102.

The static magnetic field generating magnet 102 functions as a static magnetic field generating unit generating a static magnetic field. The static magnetic field generating magnet 102 generates homogeneous static magnetic fields respectively in a direction orthogonal to the body axis of the object 101 in case of a vertical magnetic field method and in the body axis direction in case of a horizontal magnetic field method, and a static magnetic field generating source of a permanent magnet method, a normal conducting method, or a superconducting method is disposed around the object 101.

The gradient magnetic field coil 103 and the gradient magnetic field power source 106 function as a gradient magnetic field applying unit applying a gradient magnetic field to the object 101 disposed in a static magnetic field. The gradient magnetic field coil 103 is a coil wound in the three axis directions X, Y, and Z which are real space coordinate systems (static coordinate systems) of an MRI apparatus. The respective gradient magnetic field coils are connected to the gradient magnetic field power source 106 driving them to be supplied with an electric current. Specifically, the gradient magnetic field power source 106 of the respective gradient magnetic field coils is driven by receiving commands from the respective sequencers 110 to be descried, and then electric currents are supplied to the respective gradient magnetic field coils. Hence, the gradient magnetic fields Gx, Gy, and Gz are generated in the three axis directions X, Y, and Z.

For example, when a two-dimensional slice surface is imaged, a slice gradient magnetic field pulse (Gs) is applied in a direction orthogonal to a slice surface (imaging cross section) to set the slice surface for the object 101. In the other two directions which are orthogonal to the slice surface and orthogonal to each other, a phase encoding gradient magnetic field pulse (Gp) and frequency encoding (read-out) gradient magnetic field pulse (Gf) are applied to encode position information of the respective directions for an echo signal.

The transmission coil 104 and the RF transmission unit 107 function as a high-frequency magnetic field transmission unit transmitting a high-frequency magnetic field pulse (RF pulse) that excites magnetization of the object 101 at a predetermined flip angle. The transmission coil 104 is a coil irradiating an RF pulse to the object 101, is connected to the RF transmission unit 107, and is supplied with an RF pulse current from the RF transmission unit 107. By irradiating an RF pulse to the object 101 from the transmission coil 104, the NMR phenomenon is induced to atomic nuclear spins of atoms comprising the living tissues of the object 101.

Specifically, the RF transmission unit 107 is driven by receiving commands from the sequencer 110 to be described later, modulates amplitude of a high-frequency pulse, and supplies it to transmission coil 104 disposed in the vicinity of the object 101. The supplied high-frequency pulse is irradiated to the object 101 from the transmission coil 104.

The reception coil 105 and the signal detection unit 108 function as a signal reception unit receiving an echo signal generated by the object 101. The reception coil 105 is a coil receiving the NMR signal (echo signal) released by the NMR phenomenon of atomic nuclear spins comprising the living tissues of the object 101, is connected to the signal detection unit 108, and then sends the received echo signal to the signal detection unit 108. The signal detection unit 108 performs detection processing of the echo signal received by the reception coil 105.

Specifically, an echo signal of a response of the object 101 induced by an RF pulse irradiated from the transmission coil 104 is received in the reception coil 105 disposed in the vicinity of the object 101 and is sent to the signal detection unit 108. The signal detection unit 108 receives commands from the sequencer 110 to be described later, amplifies a received echo signal, divides it into two systems of orthogonal signals by quadrature phase detection, samples each of them at a determined number (such as 128, 256, and 512), converts the respective sampling signals into a digital amount by A/D conversion, and then sends them to the signal processing unit 109 to be described later. Thus, an echo signal can be obtained as time-series digital data (hereinafter, referred to as echo data) comprised of a predetermined number of sampling data.

The signal processing unit 109 performs various signal processes for echo data and sends the processed echo data to the control unit 120.

The sequencer 110 transmits various commands for data collection required for reconstructing a tomographic image of the object 101 mainly to the gradient magnetic field power source 106, the RF transmission unit 107, and the signal detection unit 108 and controls them. Specifically, the sequencer 110 operates under control of the control unit 120 to be described later, controls the gradient magnetic field power source 106, the RF transmission unit 107, and the signal detection unit 108 according to the imaging sequence, repeatedly executes applying an RF pulse and a gradient magnetic field pulse to the object 101 as well as detecting an echo signal from the object 101, and then collects echo data required for reconstructing an image in an imaging region of the object 101.

The control unit 120 performs control such as controlling the sequencer 110, processing various data, displaying process results, and saving, and includes an arithmetic processing unit having a CPU and a memory inside as well as a storage unit such as an optical disk and magnetic disk. In the present embodiment, an image is reconstructed from echo signals received by the above signal reception unit, and then commands to control operations of a gradient magnetic field application unit, a high-frequency magnetic field transmission unit, and a signal reception unit are provided to the sequencer 110 according to the imaging sequence.

Additionally, the imaging sequence is generated from an imaging parameter set by a user and a pulse sequence specified by a user.

Specifically, the sequencer 110 is controlled to collect echo data, the collected echo data is stored in a region equivalent to k-space in a memory based on encode information applied to the echo data. An echo data group stored in a region equivalent to k-space in a memory is also referred to as k-space data. Then, processes such as image reconstruction by signal processing and Fourier transform are executed for the k-space data, and an image of the object 101 that is a result of such processes is displayed on the display unit 121 to be described later as well as recorded in a storage unit.

The display unit 121 and the operation unit 122 are interfaces to communicate various control information of the MRI apparatus 100, information required for arithmetic processing, and the arithmetic processing result with a user. The MRI apparatus 100 of the present embodiment receives inputs from a user via the display unit 121 and the display unit 122. The operation unit 122 is disposed in the vicinity of the display unit 121 and controls various processes of the MRI apparatus 100 interactively through the operation unit 122 while an operator is watching the display unit 121. For example, the display unit 121 displays a reconstructed image of the object 101. Also, the operation unit 122 includes at least one of a trackball, a mouse, and a keyboard, etc. to be an input device.

Additionally, in FIG. 1(a), the transmission coil 104 and the gradient magnetic field coil 103 are installed oppositely to the object 101 in case of a vertical magnetic field method or around the object 101 in case of a horizontal magnetic field method in static magnetic field space of the static magnetic field generating magnet 102 in which the object 101 is to be inserted. Also, the reception coil 105 is installed oppositely to or around the object 101.

An imaging target nuclide of the MRI apparatus 100 is currently a hydrogen nucleus (proton) that is clinically prevalent and is a main component of the object 101. In the MRI apparatus 100, information about spatial distribution of proton density and spatial distribution of the relaxation time of an excitation state is imaged to two-dimensionally or three-dimensionally image shapes of a human head, abdomen, extremities, etc. or the functions. At this time, in MRI, an RF pulse is applied together with a gradient magnetic field to excite only a proton in a specific region.

The present embodiment adjusts each applied pulse in an imaging sequence so that only a target excitation region is selectively excited with high precision even in the three-dimensional spatial selective excitation. In prior to the description of a pulse sequence achieving the three-dimensional spatial selective excitation of the present embodiment, a pulse sequence achieving a slice selection pulse sequence and the two-dimensional spatial selective excitation will be described.

FIG. 2 shows the pulse sequence 900 to excite an arbitrary slice having a thickness in the one-dimensional direction. Hereinafter, in the pulse sequence diagrams of the present description, RF, Gx, Gy, and Gz shows application timings of an RF pulse, a gradient magnetic field in the x-axis direction, a gradient magnetic field in the y-axis direction, and a gradient magnetic field in the z-axis direction respectively. As shown in the present diagram, at the same time as the RF pulse 901, the slice selection gradient magnetic field 902 is applied to any one direction of Gx, Gy, and Gz. Here, a case of applying in the Gz direction is shown as an example. Hence, a specified predetermined slice is selectively excited only in a position in the z-axis direction.

Next, a pulse sequence (hereinafter, referred to as a 2D RF sequence) achieving the two-dimensional spatial selective excitation, the resulting k-space trajectory, and an excitation region will be described. FIG. 3(a) shows the 2D RF sequence 200, FIG. 3(b) shows the k-space trajectory 220 by the 2D RF sequence 200, and FIG. 3(c) as well as (d) show regions (the main lobe 231 and the side lobe 232) to be excited by the 2D RF sequence 200.

FIG. 3(a) shows RF, Gx, and Gy only as the 2D RF sequence 200. As shown in the present diagram, the 2D RF sequence 200 includes a two-dimensional selective excitation pulse (hereinafter, referred to as a 2D RF pulse) 201 and the oscillating gradient magnetic field pulse 202. These 2D RF pulse 201 and the oscillating gradient magnetic field pulse 202 selectively excite only a predetermined cylindrical region.

Hereinafter, the 2D RF pulse 201 as well as the oscillating gradient magnetic field pulse 202 are referred to as the two-dimensional spatial selective excitation pulse 210.

The 2D RF pulse 201 is an excitation RF pulse for a pencil-beam type exciting a cylindrical region. F0 is an irradiation frequency of the 2D RF pulse 201.

Also, as shown in FIG. 3(b), the oscillating gradient magnetic field pulse 202 is applied in the Gx and Gy directions so that the k-space trajectory 220 is a spiral trajectory from the center of the k-space to the outside or from the outside to the center. The number of oscillations n of the oscillating gradient magnetic field pulse 202 is equal to the number of spiral winds (the number of rotations) n of the k-space trajectory 220. $G_0$ is the maximum intensity of the oscillating gradient magnetic field pulse 202.

As shown in FIG. 3(c), a region to be excited by the 2D RF sequence 200 is comprised of the target excitation region (main lobe) 231 centering on the x-y plane and the non-target excitation region (side lobe) 232 in the concentric position on the outside. Transverse magnetization (signal strength) of the side lobe 232 is smaller than the main lobe 231. The diameter of the main lobe 231 to be excited is $X_0$, and the diameter of the side lobe 232 is $WX_0$. The respective excitation profiles in the x direction are shown in FIG. 3(d). The vertical axis shows the signal strength.

Next, a pulse sequence (hereinafter, referred to as a 3D RF sequence) achieving three-dimensional selective excitation of the present embodiment will be described using FIGS. 4 to 9. As described above, the 3D RF sequence applies the two-dimensional spatial selective excitation pulse 210 comprised of the 2D RF pulse 201 and the oscillating gradient magnetic field pulse 202 multiple times. At this time, strength, the number of oscillations, etc. of an RF pulse and an oscillating gradient magnetic field pulse are changed variously, and the two-dimensional spatial selective excitation pulse 210 is applied in various application patterns.

The 3D RF sequences 300 (300-1, 300-2, and 300-3) of the present embodiment are exemplified in FIG. 4(a), FIG. 6(a), and FIG. 8(a) where the application patterns of the two-dimensional spatial selective excitation pulse 210 are respectively different.

As shown in FIG. 4(a), FIG. 6(a), and FIG. 8(a), the 3D RF sequences 300 includes a plurality of the two-dimensional spatial selective excitation pulses 210 (hereinafter, referred to as the three-dimensional spatial selective excitation pulses 310 in a 3D RF sequence). The respective three-dimensional spatial selective excitation pulses 310 are comprised of the 3D RF pulse 301 that is a pencil-beam type of excitation RF pulse similar to the 2D RF pulse 201 and the oscillating gradient magnetic field pulse 302 similar to the oscillating gradient magnetic field pulse 202.

Additionally, in case of a need for separation, the respective three-dimensional spatial selective excitation pulses 310 are referred to as 310a, 310b, 310c, 310d, and 310e in order, an oscillating gradient magnetic field pulse to be applied in the x-axis direction (Gx direction) is referred to as 302x, an oscillating gradient magnetic field pulse to be applied in the y-axis direction (Gy direction) is referred to as 302y, and an oscillating gradient magnetic field pulse to be applied in the z-axis direction (Gz direction) is referred to as 302z.

As shown in FIG. 4(a), in the 3D RF sequence 300-1, the oscillating gradient magnetic field pulse 302 in the one-axis direction is a blip gradient magnetic field pulse. In an example of the present diagram, the oscillating gradient magnetic field pulses 302x and 302y are applied in the Gx and Gy directions, and the blip gradient magnetic field pulse 302z is applied in the Gz direction. Also, application intensities of the 3D RF pulse 301 is changed according to the predetermined pattern.

The k-space trajectory (the first k-space trajectory) 320-1 by the three-dimensional spatial selective excitation pulses 310 of the 3D RF sequence 300-1 is shown in FIG. 4(b). The k-space trajectories by the respective three-dimensional spatial selective excitation pulses 310a, 310b, 310c, 310d, and 310e are shown as 320a, 320b, 320c, 320d, and 320e respectively. The respective k-space trajectories 320a, 320b, 320c, 320d, and 320e are spiral trajectories on the kx-ky plane where a position in the kz direction is different.

Also, regions (the main lobe 331 and the side lobe 332) excited by the 3D RF sequence 300-1 shown in FIG. 4(a) are shown in FIGS. 5(a), 5(b), and 5(c). Additionally, 339 is a positioning image.

By the 3D RF pulse 301, the oscillating gradient magnetic field pulses 302x and 302y, and the blip gradient magnetic field pulse 302z, the voxel-shaped main lobe 331 and the ring-shaped side lobe 332-1 are excited. Also, the side lobes 332-2 and 332-3 that are the same shape as 331 and 332-1 and appear in different positions in the z-axis direction are excited. That is, according to the 3D RF sequence 300-1, the first side lobe 332-1 appears concentrically with the main lobe 331 in the directions of the oscillating gradient magnetic field pulses 302x and 302y. Also, the second side lobe 332-2 and the third side lobe 332-3 appear in the blip gradient magnetic field pulse 302z direction (Z direction). The second side lobe 332-2 and the third side lobe 332-3 are excitation regions having the same shape as the main lobe 331 and the first side lobe 332-1 respectively, and only the center position in the z direction is different. Two sets of the second side lobe 332-2 and the third side lobe 332-3 appear in positions with the same distance from the main lobe 331 in the blip gradient magnetic field pulse 302z direction (Z direction).

Also, as shown in FIG. 6(a), in the 3D RF sequence 300-2, application intensities of the 3D RF pulse 301 are all the same. On the other hand, application intensities of the oscillating gradient magnetic field pulse 302 gradually increase or decrease symmetrically for the two directions and becomes constant for the other one direction. In the present diagram, a case where the oscillating gradient magnetic field pulse 302x in the Gx direction gradually increases the intensity; the oscillating gradient magnetic field pulse 302y in the Gy direction gradually decreases the intensity; and the oscillating gradient magnetic field pulse 302z in the Gz direction makes the intensity constant is exemplified.

The k-space trajectory (the second k-space trajectory) 320-2 by the three-dimensional spatial selective excitation pulses 310 of the 3D RF sequence 300-2 is shown in FIG. 6(b) and FIG. 6(c). The respective k-space trajectories 320a, 320b, 320c, 320d, and 320e are planes orthogonal to the kx-ky plane and become respectively spiral trajectories on a different plane where the intersection lines with the kx-ky plane pass through the origin of the kx-ky plane.

Regions (the main lobe 331 and the side lobe 332) excited by the 3D RF sequence 300-2 are shown in FIGS. 7(a), 7(b), and 7(c). According to the 3D RF sequence 300-2, the voxel-shaped main lobe 331 and the disc-shaped side lobe 332-1 are excited. Also, the side lobes 332-2 and 332-3 that are the same shape as 331 and 332-1 and appear in different positions in the z-axis direction are excited.

That is, according to the 3D RF sequence 300-2, the first disc-shaped side lobe 332-1 appears on a surface identified in an application direction of an oscillating gradient magnetic field that is not applied at certain intensity. At this time, the first side lobe 332-1 appears on the xy plane. Also, the second side lobe 332-2 and the third side lobe 332-3 appear in the application direction (z direction) of an oscillating gradient magnetic field that is applied at certain intensity. The second side lobe 332-2 and the third side lobe 332-3 are excitation regions having the same shape as the main lobe 331 and the first side lobe 332-1, and only the center position in the z direction is different. Two sets of the second side lobe 332-2 and the third side lobe 332-3 appear in positions with the same distance from the main lobe 331 in an application direction (z direction) of an oscillating gradient magnetic field that is applied at certain intensity. Additionally, in FIG. 7(c), the third side lobe 332-3 is omitted.

As shown in FIG. 8(a), in the 3D RF sequence 300-3, application intensities of the 3D RF pulse 301 are all the same. At this time, the oscillating gradient magnetic field pulses 302 (302x, 302y, and 302z) are respectively applied only in two directions.

The k-space trajectory (the third k-space trajectory) 320-3 by the three-dimensional spatial selective excitation pulses 310 in the 3D RF sequence 300-3 is shown in FIGS. 8(b) to 8(d). The respective k-space trajectories 320a, 320b, and 320c become spiral trajectories on the kz-kx plane, ky-kx plane, and kz-ky plane respectively.

Regions to be excited by the 3D RF sequence 300-3 are shown in FIGS. 9(a), 9(b), and 9(c). According to the 3D RF sequence 300-3, the voxel-shaped main lobe 331 and the voxel-shaped side lobe 332-1 are excited. This creates cylinder-shaped main lobes similar to FIG. 3(c) and cylindrical side lobes in the X, Y, and Z directions according to the 3D RF sequence 300-3. Therefore, consequently, a voxel-shaped region in which a plurality of the main lobes are superimposed is excited as the main lobe 331, and a cylinder-shaped region other than 331 as well as a voxel-shaped region in which the side lobes are superimposed are excited as the side lobe 332-1.

Thus, the 3D RF sequence 300 applies the three-dimensional spatial selective excitation pulses 310 comprised of a pair of the 3D RF pulse 301 and the oscillating gradient magnetic field pulse 302 multiple times to selectively excite the voxel-shaped region. At this time, the generation mode of the k-space trajectory 320 varies depending on the application pattern of the three-dimensional spatial selective excitation pulses 310. Hence, the generation position of the side lobe 332 varies.

As described above, the present embodiment selects a k-space trajectory so that only the target excitation region is selectively excited with high precision in three-dimensional spatial selective excitation and adjusts the respective three-dimensional spatial selective excitation pulses 310 generating the selected k-space trajectory. The functions of the control unit 120 of the present embodiment to achieve this will be described. FIG. 1(b) is a functional block diagram of the control unit 120 of the present embodiment.

As shown in the present diagram, the control unit 120 of the present embodiment is comprised of the reception unit 130 receiving an imaging parameter input from a user and a selection of a k-space trajectory, the excitation region display unit 140 displaying a region to be excited by the selected k-space trajectory, the adjustment unit 150 adjusting the three-dimensional spatial selective excitation pulses 310 so that a target region is selectively excited, and the imaging unit 160 executing imaging according to the imaging sequence using the adjusted three-dimensional spatial selective excitation pulses 310.

Also, in the present embodiment, the adjustment unit 150 includes the excitation region adjustment unit 151 reflecting an adjustment for a position of an excitation region received from a user on the three-dimensional spatial selective excitation pulses 310 and the apparatus distortion adjustment unit 152 reflecting an adjustment for a shifted excitation position due to apparatus distortion on the three-dimensional spatial selective excitation pulses 310.

The reception unit 130 accepts assignments of an imaging parameter and a k-space trajectory to generate an imaging sequence to be used for main imaging. A pulse sequence having an application pattern achieving a user-selectable k-space trajectory is associated with the k-space trajectory in advance and is stored in a storage unit. The reception unit 130 extracts a pulse sequence achieving the said k-space trajectory according to the user's assignment and reflects the imaging parameter to generate the imaging sequence. The assignment, for example, is performed via an excitation region screen to be described later. At this time, it may be configured so that a user can select a k-space trajectory by displaying selectable k-space trajectories in a menu form.

The excitation region display unit 140 calculates excitation regions (the main lobe 331 and the side lobe 332) to be excited by a k-space trajectory selected by a user and displays them on the display unit 121. The display is updated each time a k-space trajectory is selected in the reception unit 130. Also, in the present embodiment, the excitation region adjustment unit 151 to be described later updates the display of the excitation regions according to the adjustment each time the adjustment by a user is reflected on the three-dimensional spatial selective excitation pulses 310.

Additionally, in the present embodiment, a screen on which the calculated main lobe 331 and the side lobe 332 are displayed is referred to as an excitation region screen. The excitation region screen includes a display area of excitation regions (the main lobe 331 and the side lobe 332), an end button receiving an intention to end excitation region adjustment, and a selection area receiving a selection of a k-space trajectory. The reception unit 130 accepts selection and change of the k-space trajectory from a user via the selection area.

In an excitation region display area, for example, an excitation area is displayed as shown in FIG. 5(a), FIG. 5(b), FIG. 5(c), FIG. 7(a), FIG. 7(b), FIG. 7(c), FIG. 9(a), FIG. 9(b), and FIG. 9(c). The display mode of the excitation region may be two-dimensional as shown in FIG. 5(a), FIG. 5(b), FIG. 7(a), FIG. 7(b), FIG. 9(a), and FIG. 9(b) or may be a three-dimensional display as shown in FIG. 5(c), FIG. 7(c), and FIG. 9(c).

Also, the display modes of the main lobe 331 and the side lobe 332 are changed so that a user understands a position of the side lobe 332 easily. Changing the display modes means, for example, to change colors or patterns, etc. Also, as shown in FIG. 5(a), FIG. 5(b), FIG. 7(a), FIG. 7(b), FIG. 9(a), and FIG. 9(b), the main lobe 331 and the side lobe 332 may be displayed on the positioning image 339.

Additionally, data displaying the default excitation regions corresponding to the respective pulse sequences is stored in a storage unit in advance.

The excitation region adjustment unit 151 accepts adjustment of an excitation region from a user via the excitation region displayed in the display unit 121 and reflects the adjustment on the three-dimensional spatial selective excitation pulses 310.

The adjustment to be accepted is, for example, the respective positions, orientations, and sizes of the main lobe 331 and the side lobe 332; the relative distance 341 between the main lobe 331 and the side lobe 332; and the relative distance 342 between the side lobes 332 (see FIG. 3(b), FIGS. 5(a) to (c), FIGS. 7(a) to (c), and FIGS. 9(a) to (c)). Additionally, the relative distances 341 and 342 are distances between the peak positions respectively.

The excitation region adjustment unit 151 adjusts the three-dimensional spatial selective excitation pulses 310 so that the adjusted main lobe 331 and side lobe 332 are achieved. Here, the three-dimensional spatial selective excitation pulses 310 are adjusted so that excitation regions displayed on an excitation region screen are achieved when an end button is pressed down. Specifically, according to changing the relative distances 341 and 342, the application number of the three-dimensional spatial selective excitation pulses 310 and the rotation number (oscillation number) of the oscillating gradient magnetic field pulses 302 are adjusted.

For example, in a case where the relative distance 341 is changed, the rotation number (oscillation number) of the respective oscillating gradient magnetic field pulses 302 is changed. The smaller the rotation number (oscillation number) of the oscillating gradient magnetic field pulses 302 is, the closer the position of the side lobe 332 is to the main lobe 331. Therefore, in a case where the relative distance 341 is lengthened, the rotation number (oscillation number) of the oscillating gradient magnetic field pulses 302 is increased.

Also, if the relative distance 342 is changed, the number of the three-dimensional spatial selective excitation pulses 310 to be applied is changed. Specifically, in case of lengthening the relative distance 342, the number of the three-dimensional spatial selective excitation pulses 310 to be applied is increased. Also, in the 3D RF sequences 300-1 and 300-2, the main lobe 331 is divided by a plurality of RF pulses (3D RF pulses 301) and excited. Therefore, if the number of the three-dimensional spatial selective excitation pulses 310 is increased, an FA of the side lobe 332-1 lowers. Accordingly, also in case of lowering the FA of the side lobe 332-1, the number of the three-dimensional spatial selective excitation pulses 310 to be applied is increased.

The apparatus distortion adjustment unit 152 reflects an excitation position shift due to apparatus distortion on the three-dimensional spatial selective excitation pulses 310.

The apparatus distortion adjustment unit 152, first, performs optimization processing similar to conventional optimization processing in the 2D RF sequence 200 for the respective three-dimensional spatial selective excitation pulses 310 to optimize an irradiation frequency, an application time, and the rotation number. Conventional optimization processing, for example, uses a method disclosed in the above PTL 1 or PTL 3. In this case, static magnetic field inhomogeneity in a region of interest is measured, and a resonance frequency of magnetization obtained from is set as an irradiation frequency of the 3D RF pulse 301. Also, while a coefficient to determine a cylinder diameter of an excitation region and a time difference to determine an offset position are being changed, an optimal application time of the 3D RF pulse 301 and the rotation number of the oscillating gradient magnetic field pulse 302 are obtained.

At this time, for example, optimization processing similar to that for the 2D RF sequence 200 is performed for one of the three-dimensional spatial selective excitation pulses 310, an obtained adjustment value for the three-dimensional spatial selective excitation pulse 310 may be applied also to the other three-dimensional spatial selective excitation pulses 310. Hence, time required for optimization adjustment can be reduced.

Additionally, the apparatus distortion adjustment unit 152 uses an excitation profile obtained from a signal measured according to a predetermined pre-scan sequence, calculates an adjustment value of the intensity (intensity adjustment value) $C_w$ of the oscillating gradient magnetic field pulse 302 and an adjustment value of the start phase (referred to as a position adjustment value or a start phase adjustment value) $C_p$ of the 3D RF pulse 301, and then reflects them on the respective three-dimensional spatial selective excitation pulses 310.

An excitation profile is obtained by performing the Fourier transform for a signal obtained according to a predetermined pre-scan sequence. The pre-scan sequence to be used is stored in a storage unit in advance according to a k-space trajectory to be used for imaging. The apparatus distortion adjustment unit 152 extracts the pre-scan sequence from the storage unit according to the k-space trajectory selected by a user.

The pre-scan sequence 400 in case of executing main imaging in the 3D RF sequence 300-1 shown in FIG. 4(a) for example is shown in FIG. 10(a). Here, an adjustment value in the blip direction (z direction) is calculated.

As shown in the present diagram, in the pre-scan sequence 400, a three-dimensional spatial selective excitation pulse (the RF pulse 401 and the oscillating gradient magnetic field pulse 402) having the same configuration as that in the sequence 300-1 shown in FIG. 4(a) excites the position of the magnetic field center (z=0) and provides the encode 403 only in the z-axis direction to obtain the signal 404. The signal 404 to be obtained has a plurality of peaks as shown in the present diagram.

Then, the Fourier transform is performed for the obtained signal 404 to obtain an excitation profile in the z direction. The excitation profile in the z direction to be obtained at this time is shown in FIG. 10(b).

When the excitation profile in the z direction is obtained, the apparatus distortion adjustment unit 152 first obtains a half-value width $WZ_1$ of an excitation profile in the z direction of the main lobe 431. Additionally, the half-value width $WZ_1$ is measured and obtained by scanning the obtained excitation profile as described in PTL 3 for example. Then, an intensity adjustment value $C_{WZ}$ of the oscillating gradient magnetic field pulse $302z$ in the z direction is calculated using the half-value width $WZ_1$. The intensity adjustment value $C_{WZ}$ is expressed using the following formula (1) by specifying a width in the z direction of the main lobe 331 set on an excitation region screen by a user as $WZ_0$.

$$C_{WZ} = WZ_1/WZ_0 \quad (1)$$

Also, a start phase adjustment value $C_{PZ}$ in the z direction is calculated by the following formula (2) using a distance $Z_1$ between the center of an excitation profile in the z direction of the obtained main lobe 431 and the magnetic field center as well as a distance $Z_0$ between an excitation profile in the z direction of the main lobe 431 and an excitation profile in the z direction of the side lobe 432.

$$C_{PZ} = 2\pi \times Z_1/Z_0 \quad (2)$$

Additionally, the start phase adjustment value $C_{PZ}$ may be calculated from a phase difference of the signal center between the signals 404 of a plurality of the obtained peaks or may be obtained by dividing a shift amount of the z direction position at peak intervals of the respective RF pulses as described in PTL 2.

The apparatus distortion adjustment unit 152 reflects the calculated oscillating gradient magnetic field intensity adjustment value $C_{WZ}$ and the start phase adjustment value $C_{PZ}$ on the three-dimensional spatial selective excitation pulses 310 in an imaging sequence. Specifically, the oscillating gradient magnetic field intensity adjustment value $C_{WZ}$ is multiplied by an intensity $Gr_0$ of the oscillating gradient magnetic field pulse $302z$ in the z direction, and the start phase adjustment value $C_{PZ}$ in the z direction is added to an increment value of a start phase of the respective 3D RF pulses 301.

Additionally, at this time, if the adjusted intensity ($Gr_0 \times C_{WZ}$) of the oscillating gradient magnetic field pulse $302z$ exceeds the maximum value of a gradient magnetic field intensity that the MRI apparatus 100 can apply, not the adjusted value but the maximum value that the MRI apparatus 100 can apply is used. In this case, it may be configured so that an excitation region by an oscillating gradient magnetic field pulse intensity to be used is calculated and displayed on the display unit 121.

Additionally, in an excitation profile by the pre-scan sequence 400, a value in which signals in the x-y direction were integrated is obtained. According to the k-space trajectory shown in FIG. 4(b), the radius 341 (a relative distance between the main lobe 331 and the side lobe 332) of the side lobe 332 is isotropic to the x-y direction, and an excitation profile in the z direction can be determined only by encoding the z direction.

Additionally, although a case where the 3D RF sequence 300-1 shown in FIG. 4(a) is used is described as an example for the above adjustment process, it is the same also for the other 3D RF sequences 300-2 and 300-3. However, in a case such as where the radius of the side lobe 332 is not isotropic to the x-y direction, an intensity adjustment value $C_W$ and a phase adjustment value $C_P$ in the respective axis directions are calculated as needed.

Figure 11:
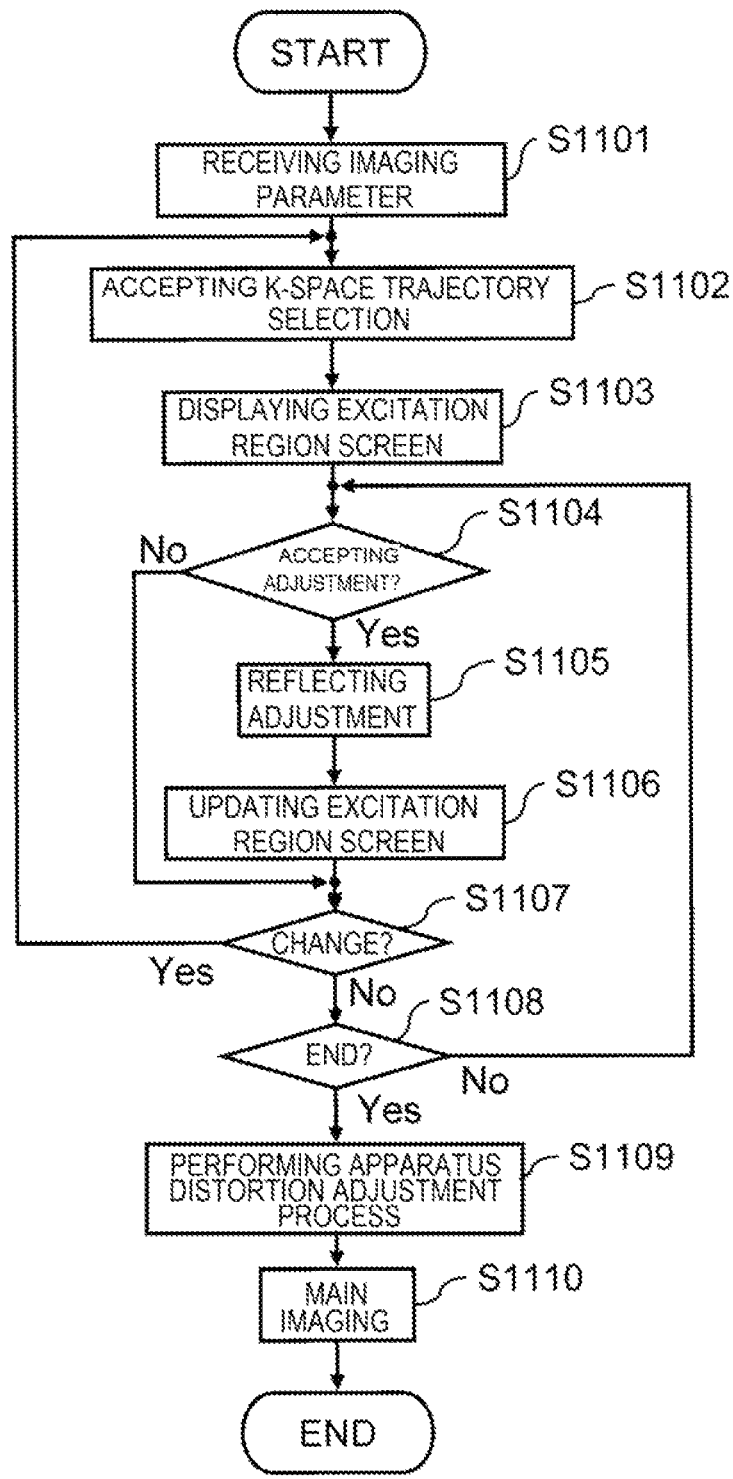
FIG. 11 is a flow chart of an imaging process in the first embodiment.

A flow of an imaging process including the respective adjustment processes described above will be described. FIG. 11 is a processing flow of an imaging process in the present embodiment. The present process starts after receiving a start command from a user.

First, the reception unit 130 receives an imaging parameter input by a user (Step S1101). Next, the reception unit 130 accepts selection of a k-space trajectory (Step S1102). When the k-space trajectory is selected, the excitation region display unit 140 generates an excitation region screen and displays an excitation region of the received k-space trajectory (Step S1103).

The excitation region adjustment unit 151 accepts adjustment from a user through an excitation region screen (Step S1104) and reflects the accepted adjustment on the three-dimensional spatial selective excitation pulses 310 (Step S1105). When the adjustment is reflected on the three-dimensional spatial selective excitation pulses 310, the excitation region display unit 140 re-calculates a region to be excited by the reflected three-dimensional spatial selective excitation pulses 310 and updates the excitation region on the excitation region screen (Step S1106).

Also, when the reception unit 130 receives a command to change a k-space trajectory from a user on the excitation region screen (Step S1107), the reception unit 130 goes back to Step 1102, receives a selected k-space trajectory, and then repeats the process.

Additionally, the adjustment reception and the change process of the k-space trajectory are continued until an end command is received from a user on the excitation region screen (Step S1108). When the end command is received from the user on the excitation region screen (Step S1108), the apparatus distortion adjustment unit 152 performs an adjustment process of an excitation position caused by apparatus distortion (the adjustment process of the apparatus distortion) (Step S1109). The flow of the adjustment process by the apparatus distortion adjustment unit 152 will be described later.

When the adjustment process by the apparatus distortion adjustment unit 152 ends, the imaging unit 160 performs main imaging (Step S1110) according to the imaging sequence by the three-dimensional spatial selective excitation pulses 310 on which the adjustment was reflected and ends the process.

Additionally, a case where adjusting an excitation region and selecting a k-space trajectory were performed in parallel was described here as an example, but is not limited to this.

It may be configured so that a k-space trajectory to be used is first determined while the respective excitation regions are being checked before an excitation region of the determined k-space trajectory is adjusted. In this case, an excitation region screen is provided with a determination button receiving an intention to determine a k-space trajectory to be used for imaging.

Figure 12:
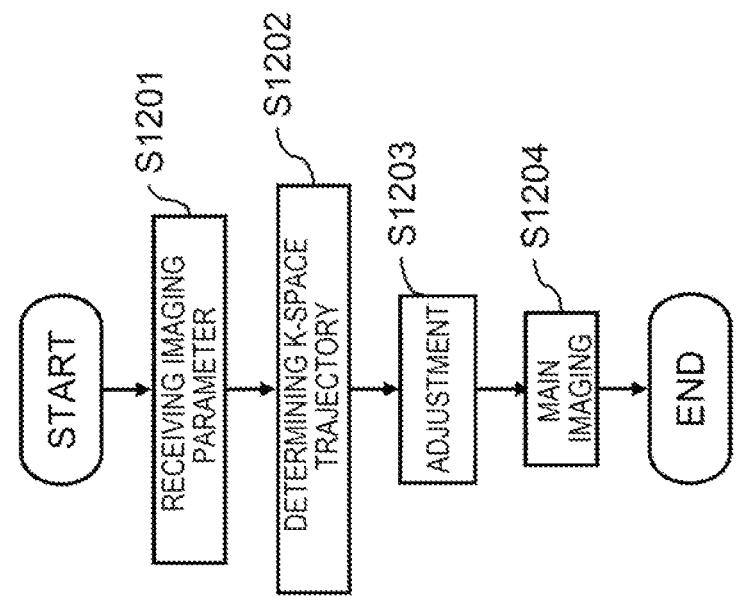
FIG. 12 is a flow chart of a variation of an imaging process in the first embodiment.

The flow of the imaging process in this case is shown in FIG. 12. First, the reception unit 130 receives an imaging parameter input from a user (Step S1201).

Next, a k-space trajectory to be used for imaging is determined (Step S1202). Here, the reception unit 130 accepts selection of a k-space trajectory, and the excitation region display unit 140 generates an excitation region screen and displays an excitation region of the received k-space trajectory. This is repeated each time the reception unit 130 receives a k-space trajectory until pressing down a determination button is accepted. The selection is stored in a storage unit in advance and is performed from among multiple 3D RF sequences (k-space trajectories) in which application patterns of the three-dimensional spatial selective excitation pulses 310 are different.

Then, the adjustment unit 150 adjusts the three-dimensional spatial selective excitation pulses 310 of the determined k-space trajectory (Step S1203). Here, the adjustment is performed so that a target region is excited selectively. The two types of adjustments for an excitation position in accordance with a user's command as described above and for apparatus distortion are performed. Then, the imaging unit 160 executes main imaging according to the imaging sequence after adjusting the three-dimensional spatial selective excitation pulses 310 (Step S1204).

Figure 13:
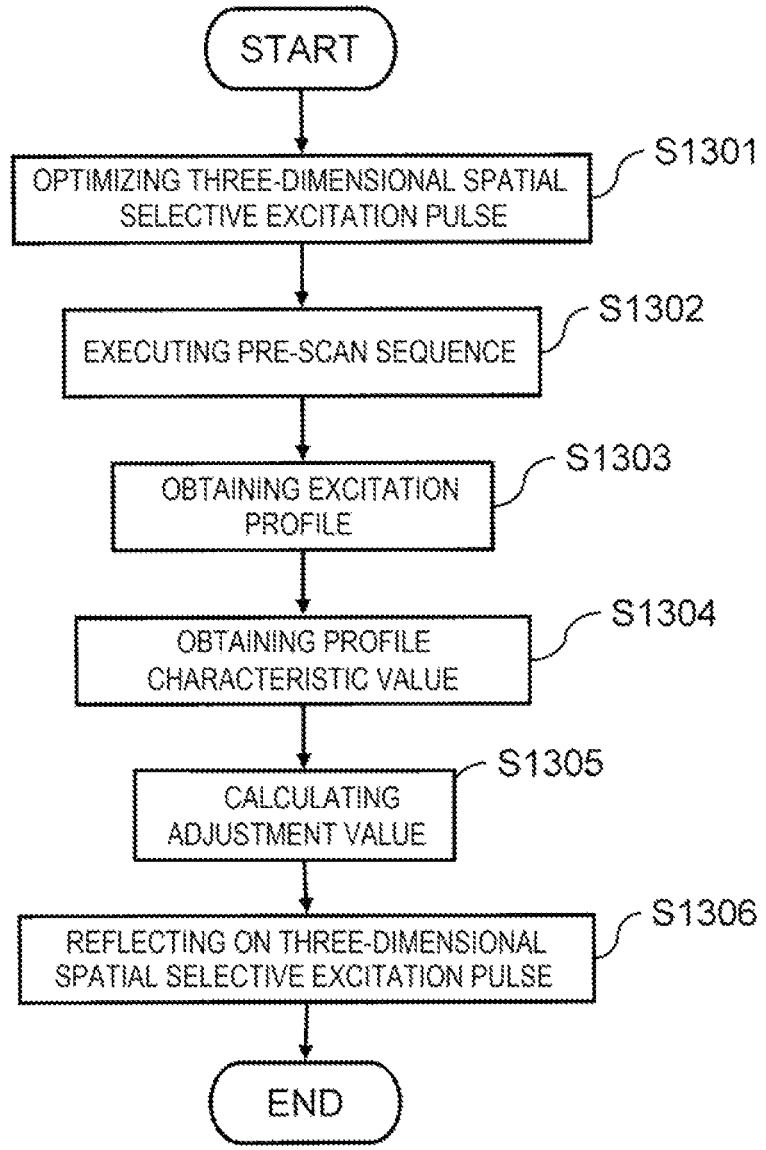
FIG. 13 is a flow chart of adjustment processing of apparatus distortion in the first embodiment.

Next, the flow of an adjustment process of apparatus distortion by the apparatus distortion adjustment unit 152 will be described. FIG. 13 is a process flow of the adjustment process of the apparatus distortion in the present embodiment.

The apparatus distortion adjustment unit 152 performs optimization processing optimizing the respective three-dimensional spatial selective excitation pulses 310 (Step S1301). The optimization processing is performed using the above method (optimization processing for the two-dimensional spatial selective excitation pulses 210 in a conventional 2D RF sequence).

Next, the apparatus distortion adjustment unit 152 selects a pre-scan sequence according to a k-space trajectory to obtain a signal (Step S1302). Then, an excitation profile is obtained from the obtained signal (Step S1303).

Next, characteristic values of the excitation profile are obtained (Step S1304). For example, in a case where the selected k-space trajectory is the first k-space trajectory 320-1 shown in FIG. 4(b) and the excitation profile is that obtained by the pre-scan sequence 400 shown in FIG. 10(a), the characteristic values to be obtained are a half-value width $WZ_1$ in the z direction of the excitation profile of the main lobe 431; a distance $Z_1$ in the z direction between the peak position of the excitation profile of the main lobe 431 and the magnetic field center; and a distance $Z_0$ in the z direction between the peak position of excitation profile of the main lobe 431 and the peak position of the excitation profile of the side lobe 432 as shown in FIG. 10(b).

Then, using the obtained respective characteristic values, an intensity adjustment value $C_W$ of the oscillating gradient magnetic field pulse 302 in an axis direction required according to a k-space trajectory and a start phase adjustment value $C_P$ of the 3D RF pulse 301 are calculated (Step S1305). These calculated adjustment values are reflected on the three-dimensional spatial selective excitation pulses 310 (Step S1306).

As described above, the MRI apparatus 100 of the present embodiment is the MRI apparatus 100 having the control unit 120 that controls the respective units of the apparatus according to an imaging sequence generated with a previously set imaging parameter and a predetermined pulse sequence, wherein the pulse sequence includes a multi-dimensional spatial selective excitation pulse comprised of an oscillating gradient magnetic field pulse and a two-dimensional selective excitation pulse having a main lobe and a side lobe, and the control unit 120 includes the adjustment unit 150 adjusting the multi-dimensional spatial selective excitation pulse so that the main lobe selectively excites a target region.

The pulse sequence may be the three-dimensional selective excitation sequence 300 applying a plurality of the multi-dimensional spatial selective excitation pulses.

Also, the control unit 120 may further include the reception unit 130 accepts user selection from a plurality of the three-dimensional selective excitation sequences 300 whose application patterns of the multi-dimensional spatial selective excitation pulses are different and the excitation region display unit 140 displaying excitation regions of the main lobe and the side lobe of the said three-dimensional selective excitation sequence 300 each time a user selects the three-dimensional selective excitation sequence 300.

At this time, the excitation region display unit 140 may display the excitation regions on a positioning image.

Also, the adjustment unit 150 may include the excitation region adjustment unit 151 that accepts adjustment of an excitation region from a user on the excitation regions to be displayed and reflects the said adjustment on the multi-dimensional spatial selective excitation pulses.

Also, the adjustment unit 150 includes the apparatus distortion adjustment unit 152 adjusting the multi-dimensional spatial selective excitation pulses so that influence by apparatus distortion is removed based on an excitation profile by a signal obtained in a predetermined pre-scan, and the apparatus distortion adjustment unit 152 calculates an intensity adjustment value of the oscillating gradient magnetic field pulse 202 and a start phase adjustment value of the respective two-dimensional selective excitation pulses 201 from the excitation profile and may adjust the multi-dimensional spatial selective excitation pulses using the calculated intensity adjustment value and start phase adjustment value.

The intensity adjustment value may be calculated as a ratio of a half-value width of the excitation profile of a main lobe and a width in the same direction of a target excitation region, and the start phase adjustment value may be calculated as a ratio of a distance between the center of the excitation profile of the main lobe and the magnetic field center and a distance between the center of the excitation profile of the main lobe and the center of the excitation profile of a side lobe.

The excitation region adjustment unit 151 may adjust the oscillation number of the oscillating gradient magnetic field pulses so that the number becomes larger as a relative distance between the main lobe and the side lobe becomes longer and adjust the application number of the multi-dimensional spatial selective excitation pulses so that the number becomes larger as a relative distance between the side lobes becomes longer.

Therefore, according to the present embodiment, an excitation region is displayed in a user-friendly mode even if imaging uses a 3D RF sequence. While checking the display, a user can select a k-space trajectory where a position without an examination problem is excited (an application pattern of the three-dimensional spatial selective excitation pulses 310. Additionally, while checking the display, the user can adjust sizes and positions of a main lobe and a side lobe. Also, the adjustment results are automatically reflected on an imaging sequence.

That is, according to the present embodiment, even if imaging uses a 3D RF sequence, a user can easily adjust an imaging range, an imaging target, and a positional relationship of a main lobe and a side lobe to change a generation point of a side lobe to a position without an examination problem. Therefore, according to the present embodiment, even if imaging uses a 3D RF sequence, an excitation in a non-target region by the side lobe can be avoided easily.

Also, according to the present embodiment, an excitation position shift by apparatus distortion is adjusted in accordance with a k-space trajectory (an application pattern of a three-dimensional spatial selective excitation pulse). Therefore, even in case of a 3D RF sequence that has a longer application time of the three-dimensional spatial selective excitation pulse, the excitation position shift by apparatus distortion can be reduced similarly to imaging by a 2D RF sequence. That is, according to the present embodiment, even in case of a 3D RF sequence, a target region can be excited stably.

Hence, the excitation is different from a target, which can reduce cases where an examination fails. Also, even in an image to be obtained, artifacts due to a signal of a non-target region can be reduced, which results in improving image quality.

Therefore, according to the present embodiment, even in case of a two-dimensional spatial selective excitation method or a three-dimensional spatial selective excitation method, only a target region can be selectively excited with high precision without burdening users, which reduces examination fails as well as improves quality of images to be obtained.

Additionally, the present embodiment is configured so that a user selects an imaging sequence (k-space trajectory) to be used for imaging, but is not limited to this. For example, it may be configured so that a system automatically determines based on imaging conditions set by a user. In this case, the control unit 120 further includes the sequence determination unit 170 as shown in FIG. 14(a). The sequence determination unit 170 determines the three-dimensional selective excitation sequence 300 optimal for the said imaging conditions from among a plurality of the three-dimensional selective excitation sequences 300 in which application patterns of the multi-dimensional spatial selective excitation pulses are different based on the imaging conditions.

For example, in a 3D RF sequence, it is the most difficult to increase the application number of the three-dimensional spatial selective excitation pulses 310. Therefore, a side lobe to be generated in a direction where the number of trajectories increases or decreases according to the application number comes nearest to a main lobe easily. For example, in case of using the k-space trajectory 320-1 shown in FIG. 4(b), the side lobe 332-2 in the z direction shown in FIG. 5(b) appears nearest to the main lobe 331. On the other hand, there are three encoding directions of a slice direction, a phase direction, and a read-out direction in 3D imaging, and aliasing does not appear in the read-out direction of a reconstructed image.

Therefore, the sequence determination unit 170 selects a pulse sequence showing a k-space trajectory in which a read-out direction of an imaging sequence is a direction whose number of trajectories increases or decreases according to the number of applications (a direction where a side lobe easily comes to the nearest).

At this time, aliasing in a read-out direction can be ignored, and a side lobe position in the same direction is unnecessary. Therefore, because displaying the side lobe in the same direction in an excitation region displayed on an excitation screen is unnecessary, the visibility is improved.

Additionally, in this case, the reception unit 130 receives only an imaging parameter.

Also, a system is not determined automatically, and it may be configured so that an encoding direction and a k-space trajectory that the system recommends for operator settings are presented to accept selection from the operator. In this case, the control unit 120 determines at least either one of the encoding direction and the k-space trajectory as a recommended change plan as shown in FIG. 14(b) to present it to the operator and further includes the change plan presentation unit 180 accepting designation from the operator.

The change plan presentation unit 180 analyzes the received imaging conditions and the three-dimensional selective excitation sequence 300 to create and present the said imaging conditions or a change plan of the said three-dimensional selective excitation sequence 300. At this time, the three-dimensional selective excitation sequence 300 to be used for imaging and the change plan are selected from among a plurality of the three-dimensional selective excitation sequences 300 whose application patterns of the multi-dimensional spatial selective excitation pulses to be kept in advance are different.

For example, the change plan presentation unit 180 analyzes imaging conditions set by a user and a k-space trajectory and creates the following change plan if a direction whose number of trajectories increases or decreases according to the number of applications (a direction where a side lobe easily comes to the nearest) is determined to be a slice direction or a phase encoding direction (different from a read-out encoding direction) to present the change plan to the user by displaying it on the display unit 121.

1) An encoding direction is changed so that a direction whose number of trajectories increases or decreases according to the number of applications (a direction where a side lobe easily comes to the nearest) of a k-space trajectory set by a user becomes a read-out encoding direction.

2) A k-space trajectory is changed so that a read-out direction of imaging conditions set by the user becomes a direction whose number of trajectories increases or decreases according to the above number of applications (a direction where a side lobe easily comes to the nearest).

3) Imaging is performed as is.

Additionally, according to the choice of 3), an examination fail caused by an operator exciting an unintentional region can be prevented.

In this case, the reception unit 130 accepts selection by a user from among change plans presented by the change plan presentation unit 180 and determines an imaging parameter and a k-space trajectory to be used for imaging based on the received change plan. The excitation region display unit 140 calculates and displays an excitation region according to the determined imaging parameter and k-space trajectory. The adjustment unit 150 specifies the three-dimensional spatial selective excitation pulses 310 determined by the determined imaging parameter and k-space trajectory as an adjustment target.

Second Embodiment

Next, the second embodiment applying the present invention will be described. The first embodiment prevents a signal inflow from a non-target region by adjusting a position of an excitation region. On the contrary to this, the present embodiment prevents the signal inflow from the non-target region by restricting a side lobe itself.

The configuration of the MRI apparatus 100 of the present embodiment is basically similar to the first embodiment. However, the present embodiment further provides a two-dimensional spatial selective excitation pulse with the second 2D RF pulse (hereinafter, a sub 2D RF pulse) and restricts a side lobe properly by the sub 2D RF pulse. Therefore, pulse sequences to be used for imaging vary in the present embodiment.

Also, the control unit 120 of the present embodiment, as shown in FIG. 15(a), includes the reception unit 130 accepts an imaging parameter input from a user; the adjustment unit 150 adjusting a two-dimensional spatial selective excitation pulse so that a target region is excited selectively; and the imaging unit 160 executing imaging according to an imaging sequence in which the adjusted two-dimensional spatial selective excitation pulse is used. Then, the adjustment unit 150 includes the sub-pulse adjustment unit 153 adjusting so that a sub 2D RF pulse cancels out a side lobe of a 2D RF pulse. A configuration with the same name as the first embodiment basically has similar functions. Hereinafter, the present embodiment will be described by focusing on a configuration different from the first embodiment.

First, a pulse sequence of the present embodiment will be described. Here, a 2D RF sequence is taken as an example for the description. FIG. 16(a) is an example of the 2D RF sequence 500. Here, only Gx and Gy are shown as gradient magnetic field application axes.

As shown in the present diagram, the 2D RF sequence 500 of the present embodiment includes the 2D RF pulse 501, the second 2D RF (hereinafter, a sub 2D RF pulse) 501s, and the oscillating gradient magnetic field pulse 502. Also in the present embodiment, the 2D RF pulse 501, the second 2D RF pulse 501s, and the oscillating gradient magnetic field pulse 502 are collectively referred to as the two-dimensional spatial selective excitation pulse 510. Additionally, the present diagram shows the 2D RF pulse 501 on the RF1 axis and the sub 2D RF pulse 501s on the RF2 axis.

The 2D RF pulse 501 is an RF pulse of pencil-beam type excitation similarly to the 2D RF pulse of the first embodiment. The irradiation frequency is specified as F0. Also, the application start phase is specified as 90 degrees.

On the other hand, the sub 2D RF pulse 501s specifies the application start phase as −90 degrees and the irradiation frequency as F0+ΔF. A main lobe by the sub 2D RF pulse 501s is concentric. ΔF is determined so that the main lobe is in the same position as a side lobe by the 2D RF pulse. The determination method will be described later.

Also, if the intensity and the oscillation number of the oscillating gradient magnetic field pulse 202 of the 2D RF sequence 200 described in the first embodiment were specified as $G_0$ and n respectively, the intensity and the oscillation number of the oscillating gradient magnetic field pulse 502 are specified as $2G_0$ and n/2 respectively.

Hereinafter, the ΔF determination method of the sub 2D RF pulse 501s will be described.

It is known that the radius of a side lobe becomes half when the oscillation number of an oscillating gradient magnetic field pulse becomes half while the size of a main lobe is kept constant in a sequence in which a pencil-beam type RF pulse is used (for example, see NPTL 2).

Therefore, taking the diameter of the main lobe 231 by the two-dimensional spatial selective excitation pulses 210 (an irradiation frequency F0 of the 2D RF pulse 201, the maximum intensity of the oscillating gradient magnetic field pulse 202, and a rotation number n) in the 2D RF sequence 200 described in the first embodiment as $X_0$ as well as the diameter of the side lobe 232 as $WX_0$ as shown in FIG. 3(c) and taking the diameter of the main lobe 531 by the 2D RF pulse 501 of the two-dimensional spatial selective excitation pulse 510 in the 2D RF sequence 500 of the present embodiment as $X_1$ as well as the diameter of the side lobe 532 as $WX_1$, the following formulas (3) and (4) are established.

$$X_1 = X_0 \quad (3)$$

$$WX_1 = WX_0/2 \quad (4)$$

An excitation profile in the x direction of the main lobe 531 by the 2D RF pulse 501 and that of the side lobe 532 are shown in FIG. 16(c).

Here, in case of keeping a scanning speed of a k-space, specifying TBW (Time Band Width) as $TBW_1$ and Duration as T of the sub 2D RF pulse 501s, and specifying an irradiation frequency as F0+ΔF and an application start phase as −90 degrees as described above, a main lobe by the sub 2D RF pulse 501s is concentric, and the diameter is expressed as $4X_0 T\Delta F/TBW_1$. Hence, an excitation profile s of the main lobe 531s by the sub 2D RF pulse 501s becomes the one shown in FIG. 16(c). The reason why it is opposite to the side lobe 532 by the 2D RF pulse 501 is because a start phase of the sub 2D RF pulse 501s is shifted 180 degrees from a start phase of the 2D RF pulse 501.

Therefore, when ΔF is determined so that a diameter $WX_1$ of the side lobe 532 by the 2D RF pulse 501 is equal to a diameter $4X_0 T\Delta F/TBW_1$ of the main lobe 531s of the sub 2D RF pulse 501s, the side lobe 532 by the 2D RF pulse 501 and the main lobe 531s of the sub 2D RF pulse 501s are in the same position as shown in FIG. 16(b).

That is, ΔF is determined so that the following formula (5) is transformed to meet the following formula (6).

$$WX_1 = 4X_0 T\Delta F/TBW_1 \quad (5)$$

$$\Delta F = WX_0 TBW_1/(8X_0 T) \quad (6)$$

Next, an adjustment process of a sub 2D RF pulse by the sub-pulse adjustment unit 153 of the present embodiment will be described.

In the present embodiment, the side lobe 532 by the 2D RF pulse 501 is cancelled out by the main lobe 531s by the sub 2D RF pulse 501s. Therefore, the diameters (generation positions) and intensities of the side lobe 532 and the main lobe 531s need to correspond precisely. Therefore, the sub-pulse adjustment unit 153 of the present embodiment first optimizes the 2D RF pulse 501 and the oscillating gradient magnetic field pulse 502 in a similar method to the optimization method of the first embodiment, and then optimizes the sub 2D RF pulse 501s so that the diameters and intensities of the side lobe 532 and the main lobe 531s correspond with each other. Additionally, a shift amount ΔF from the 2D RF pulse 501 at an irradiation frequency of the sub 2D RF pulse 501s is to be determined in the above method.

Hereinafter, the flow of a sub-pulse adjustment process by the above sub-pulse adjustment unit 153 will be described.

Figure 17:
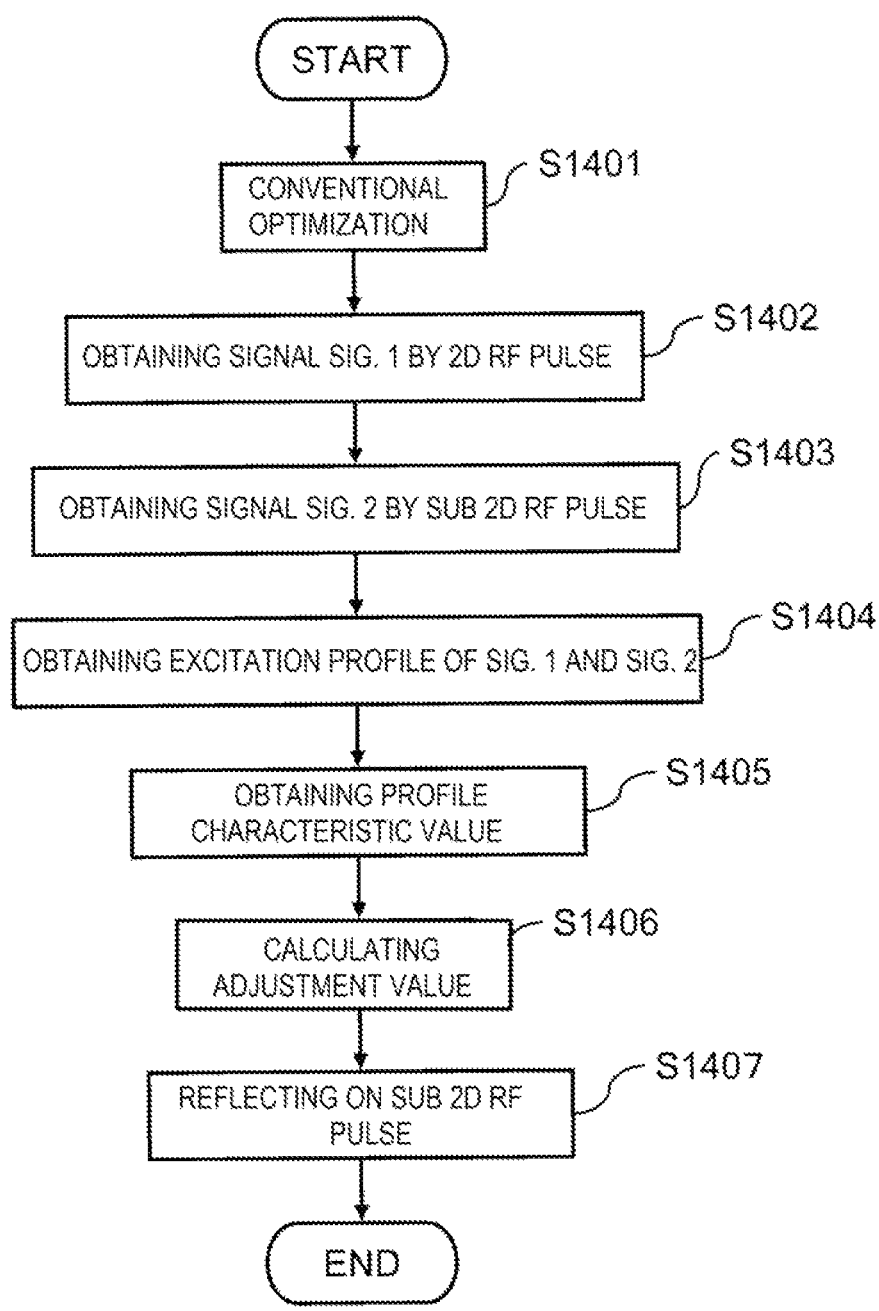
FIG. 17 is a flow chart of a sub-pulse adjustment process in the second embodiment.

FIG. 17 is the processing flow of the sub-pulse adjustment process of the present embodiment.

First, an optimization process is performed for the 2D RF pulse 501 and the oscillating gradient magnetic field pulse 502 in the two-dimensional spatial selective excitation pulse 510 in a similar method to Step S1301 of the first embodiment (Step S1401). Here, the optimization is performed by irradiating the 2D RF pulse 501 only as an RF pulse.

Next, an adjustment process is performed for the sub 2D RF pulse 501s. The pre-pulse sequence 600 to be used for this adjustment process is shown in FIG. 18(a).

First, the signal Sig. 1 by the 2D RF pulse 501 is obtained (Step S1402). Here, as shown in FIG. 18(a), the same pulse as the 2D RF pulse 501 and the oscillating gradient magnetic field pulse 502 is applied to excite the position (X, Y)=(0, 0). That is, the 90° pulse 601 is irradiated at an irradiation frequency F0, and the oscillating gradient magnetic field pulse 602 is applied in two directions. Here, a case of applying in the Gx and Gy directions is exemplified. Next, a slice selection type of the 180° pulse 603 is applied to a cross-section parallel to the pencil-beam axis direction. Here, the 180° pulse 603 is applied together with the slice selection gradient magnetic field pulse 604 in the x direction. Additionally, the read-out gradient magnetic field pulse 606 is applied in a direction (the y direction in FIG. 18(a)) parallel to a slice surface that is vertical and 180° in the pencil-beam axis direction to obtain the signal 605.

Next, the signal Sig. 2 by the sub 2D RF pulse 501s is obtained in a similar method to Step S1302 (Step S1403). However, an irradiation frequency of the pulse 601 is specified as F0+ΔF.

The Fourier transform is performed for Sig. 1 and Sig. 2 respectively to obtain the excitation profile 620 in the diameter direction (y direction) of a pencil beam of the 2D RF pulse 501 and the excitation profile 630 in the diameter direction (y direction) concentric with the sub 2D RF pulse 501s (Step S1404). The excitation profiles 620 and 630 obtained at this time are shown in FIGS. 18(b) and 18(c) respectively.

Using the diameter $WY_1$ of a side lobe by the 2D RF pulse 501 and the diameter $WY_2$ of a main lobe by the sub 2D RF pulse 501s obtained respectively from the excitation profiles 620 and 630, a frequency adjustment value $C_{F2}$ of the sub 2D RF pulse 501s is calculated so that both the diameters correspond with each other. Also, using the maximum value $SI_1$ of a signal strength of the side lobe by the 2D RF pulse 501 and the maximum value $SI_2$ of a signal strength of the main lobe by the sub 2D RF pulse 501s, an intensity adjustment value $C_{A2}$ of the sub 2D RF pulse 501s is calculated so that both the maximum values correspond with each other (Step S1406).

Here, the calculation is performed according to the following formulas (7) and (8) respectively.

$$C_{F2} = WY_1/WY_2 \quad (7)$$

$$C_{A2} = SI_1/SI_2 \quad (8)$$

Then, the calculated frequency adjustment value $C_{F2}$ and intensity adjustment value $C_{A2}$ are reflected on the sub 2D RF pulse 501s (Step S1407). Specifically, a frequency adjustment value $C_{F2}$ is multiplied by ΔF to specify an irradiation frequency of the sub 2D RF pulse 501s as (F0+$C_{F2}$ΔF). Also, an adjustment value $C_{A2}$ is multiplied by a strength $Amp_2$ of the sub 2D RF pulse 501s to specify a strength of the sub 2D RF pulse 501s as ($C_{A2}Amp_2$).

By using the above adjustment method, a 2D RF pulse can be optimized even when two types of frequencies are output simultaneously. An excitation position can be controlled precisely even in a case where there is a difference between two irradiation systems.

Also, the above adjustment cancels out the side lobe 532 by the 2D RF pulse 501 and the main lobe 531s by the sub 2D RF pulse 501s, which can reduce a signal value of the said region to almost 0 as shown in FIG. 16(b).

Here, the flow of an imaging process of the present embodiment will be described. FIG. 15(b) is the process flow of an imaging process of the present embodiment.

First, the reception unit 130 accepts an imaging parameter input from a user (Step S1501).

Next, the sub-pulse adjustment unit 153 optimizes the 2D RF pulse 501 and the oscillating gradient magnetic field pulse 502 in the above method as well as performs adjustment of the sub 2D RF pulse 501s (Step S1502). Here, as described above, an application strength and an irradiation frequency of the sub 2D RF pulse 501s are adjusted so that a main lobe by the sub 2D RF pulse 501s cancels out a side lobe by the 2D RF pulse 501.

Then, the imaging unit 160 performs main imaging using the adjusted two-dimensional spatial selective excitation pulse (Step S1503).

Additionally, a pulse sequence to be used for main imaging may be a 3D RF sequence. In the 3D RF sequence 300, the respective three-dimensional spatial selective excitation pulses 310 are provided with the above sub 2D RF pulse 501s. In this case, instead of the above optimization process (Step S1401) by the sub-pulse adjustment unit 153, an apparatus distortion adjustment process of the first embodiment is executed to perform optimization and adjustment for the 3D RF pulse 301 and the oscillating gradient magnetic field pulse 302. Then, the sub-pulse adjustment unit 153 adjusts the sub 2D RF pulse 501s of the respective three-dimensional spatial selective excitation pulses 310 in the above method.

Also, in case of using a 3D RF sequence, it may be configured so that an excitation region adjustment process is performed by providing the excitation region adjustment unit 151 similarly to the first embodiment. Also, similarly to the first embodiment, it may be configured so that the reception unit 130 and the excitation region display unit 140 accept selection of a desired k-space trajectory.

Also, in case of using a 3D RF sequence, the sequence determination unit 170 or the change plan presentation unit 180 may be provided similarly to the first embodiment.

As described above, the MRI apparatus 100 of the present embodiment is provided with a control unit controlling the respective units of the apparatus according to an imaging sequence generated by a preset imaging parameter and a predetermined pulse sequence, the pulse sequence is provided with multi-dimensional spatial selective excitation pulses comprised of the two-dimensional spatial selective excitation pulse 501 having a main lobe and a side lobe as well as the oscillating gradient magnetic field pulse 502, and the control unit 120 is provided with the adjustment unit 150 adjusting the multi-dimensional spatial selective excitation pulses so that the main lobe selectively excites a target region.

At this time, the multi-dimensional spatial selective excitation pulses is further provided with the sub-two-dimensional selective excitation pulse 501s to be applied together with the two-dimensional spatial selective excitation pulse 501, and the adjustment unit 150 is provided with the sub-pulse adjustment unit 153 determining an application strength and an irradiation frequency of the said sub-two-dimensional selective excitation pulse 501s so that a main lobe by the sub-two-dimensional selective excitation pulse 501s cancels out a side lobe by the two-dimensional spatial selective excitation pulse 501.

At this time, a start phase of the sub-two-dimensional selective excitation pulse 501s may be different by 180 degrees from a start phase of the two-dimensional selective excitation pulse 501.

Also, the oscillation number of the oscillating gradient magnetic field pulse 502 may be smaller than that of the oscillating gradient magnetic field pulse 202 of multi-dimensional spatial selective excitation pulses that obtain the same main lobe and is not provided with the sub-two-dimensional selective excitation pulse 501s.

Thus, according to the present embodiment, a main lobe by a sub 2D RF pulse can cancel out a side lobe by a 2D RF pulse by applying the sub 2D RF pulse obtaining a concentric excitation region together with the 2D RF pulse. Therefore, according to the present embodiment, an excitation in a non-target region by the side lobe can be avoided easily without burdening users even in case of imaging using either of a 2D RF sequence or 3D RF sequence. Hence, influence that the side lobe has on image quality can be restricted.

Also, similarly to the first embodiment, an excitation position shift due to apparatus distortion can be reduced, which can excite a target region stably. A case where an examination fails with an excitation different from the purpose can be reduced. Also, artifacts due to a signal of a non-target region can be reduced for an image to be obtained, which improves image quality.

Generally, in a sequence where a two-dimensional spatial selective excitation pulse is used, a pencil-beam type of RF pulse exciting a cylindrical region only is used. At this time, a gradient magnetic field (oscillating gradient magnetic field) pulse is provided so as to have a spiral trajectory from the center of a k-space to the outside or from the outside to the center. Therefore, an application time of the two-dimensional spatial selective excitation pulse becomes long. Particularly, in a 3D RF sequence where the two-dimensional spatial selective excitation pulse is applied multiple times, the application time becomes longer.

In order to make the application time short, for example, it is thought that a size of a main lobe is kept constant to halve the rotation number of the k-space. However, in a sequence where the pencil-beam type of RF pulse is used, a side lobe is generated in addition to the main lobe as described above.

For example, if the rotation number of the k-space (the winding number of the spiral trajectory) is halved while the size of the main lobe is kept constant, the application time can be shortened by half, but it is known that the radius of the side lobe is also halved (for example, see NPTL 2). In a case where the radius of the side lobe gets smaller and is close to the main lobe, there is a possibility that the side lobe can be superimposed on an imaging region.

Also, as a method to shorten the RF pulse application time, a method to create an irradiation waveform of an optimum and shortest RF pulse from irradiation sensitivity distribution, a k-space trajectory, a target excitation profile of the transmission coil 104 with a plurality of channels is known (for example, see NPTL 3). However, when the sensitivity distribution of the transmission coil 104 is used for creating the RF pulse waveform, irradiation inhomogeneity is caused in a case where a change of object-dependent sensitivity distribution etc. occurs. Also, the RF waveform needs to be changed depending on the pattern of the transmission coil 104, which results in an extremely complicated system configuration.

As described above, according to the present embodiment, the rotation number of the k-space can be reduced while the main lobe diameter is kept constant by simultaneously applying RF pulses with two types of frequencies. At this time, according to the present embodiment, the sensitivity distribution of the transmission coil 104 is not used. Therefore, as described above, an examination time can be shortened without the irradiation inhomogeneity caused by using the sensitivity distribution, the complication of the system configuration, etc. in the present embodiment.

As described above, the present embodiment can reduce influence by a side lobe without adjustment from a user or by shortening a measurement time. Hence, "Duration" can be shortened without changing the side lobe diameter and performing complicated calculation using irradiation sensitivity distribution.

Additionally, although the oscillation number of the oscillating gradient magnetic field pulse 502 is a half of that of the first embodiment, the oscillation number of the oscillating gradient magnetic field pulse 502 is not limited to this in the present embodiment. There is no problem if a side lobe is not superimposed on a main lobe.

DESCRIPTION OF REFERENCE NUMERALS

100: MRI apparatus, 101: object, 102: static magnetic field generating magnet, 103: gradient magnetic field coil, 104: transmission coil, 105: reception coil, 106: gradient magnetic field power source, 106: signal detection unit, 107: RF transmission unit, 108: signal detection unit, 109: signal processing unit, 110: sequencer, 110: measurement control unit, 111: bed, 120: control unit, 121: display unit, 122: operation unit, 130: reception unit, 140: excitation region display unit, 150: adjustment unit, 151: excitation region adjustment unit, 152: apparatus distortion adjustment unit, 153: sub-pulse adjustment unit, 160: imaging unit, 170: sequence determination unit, 180: change plan presentation unit, 200: 2D RF sequence, 201: 2D RF pulse, 202: oscillating gradient magnetic field pulse, 210: two-dimensional spatial selective excitation pulses, 220: k-space trajectory, 231: main lobe, 232: side lobe, 300: 3D RF sequence, 300: three-dimensional selective excitation sequence, 301: 3D RF pulse, 302: oscillating gradient magnetic field pulse, 302x: oscillating gradient magnetic field pulse, 302y: oscillating gradient magnetic field pulse, 302z: oscillating gradient magnetic field pulse, 310: three-dimensional spatial selective excitation pulses, 320: k-space trajectory, 331: main lobe, 332: side lobe, 341: relative distance, 342: relative distance, 400: pre-scan sequence, 401: RF pulse, 402: oscillating gradient magnetic field pulse, 403: encode, 404: signal, 431: main lobe, 432: side lobe, 500: 2D RF sequence, 501: 2D RF pulse, 501: two-dimensional spatial selective excitation pulse, 501s: sub 2D RF pulse, 501s: sub-two-dimensional selective excitation pulse, 502: oscillating gradient magnetic field pulse, 510: two-dimensional spatial selective excitation pulse, 531: main lobe, 531s: main lobe, 532: side lobe, 600: pre-pulse sequence, 601: 90° pulse, 602: oscillating gradient magnetic field pulse, 603: 180° pulse, 604: slice selection gradient magnetic field pulse, 605: signal, 606: read-out gradient magnetic field pulse, 620: excitation profile, 630: excitation profile, 900: pulse sequence, 901: RF pulse, 902: slice selection gradient magnetic field

The invention claimed is:

1. A magnetic resonance imaging apparatus including:
a control unit controlling the respective units of the apparatus according to an imaging sequence generated by a preset imaging parameter and a predetermined pulse sequence,
wherein the pulse sequence includes multi-dimensional spatial selective excitation pulses comprised of a two-dimensional selective excitation pulse having a main lobe and a side lobe as well as an oscillating gradient magnetic field pulse as pulses to be applied, and
the control unit includes an adjustment unit adjusting the multi-dimensional spatial selective excitation pulses so that the main lobe selectively excites a target region.

2. The magnetic resonance imaging apparatus according to claim 1,
wherein the pulse sequence is a three-dimensional selective excitation sequence in which a plurality of the multi-dimensional spatial selective excitation pulses are applied.

3. The magnetic resonance imaging apparatus according to claim 2,
wherein the control unit further includes a reception unit accepting selection from a user from among a plurality of the three-dimensional selective excitation sequences whose application patterns of the multi-dimensional spatial selective excitation pulses are different and an excitation region display unit displaying excitation regions of the main lobe and the side lobe of the said three-dimensional selective excitation sequence each time a user selects the three-dimensional selective excitation sequence.

4. The magnetic resonance imaging apparatus according to claim 1,
wherein the control unit further includes an excitation region display unit displaying excitation regions of the main lobe and the side lobe, and
the adjustment unit accepts excitation region adjustment from a user on the excitation regions to be displayed and includes an excitation region adjustment unit reflecting the said adjustment on the multi-dimensional spatial selective excitation pulses.

5. The magnetic resonance imaging apparatus according to claim 1,
wherein the adjustment unit includes an apparatus distortion adjustment unit adjusting the multi-dimensional spatial selective excitation pulses so that influence by apparatus distortion is removed based on an excitation profile by a signal obtained in a predetermined pre-scan, and
the apparatus distortion adjustment unit calculates an intensity adjustment value of the oscillating gradient magnetic field pulse and a start phase adjustment value of the respective two-dimensional selective excitation pulses from the excitation profile to adjust the multi-dimensional spatial selective excitation pulses using the calculated intensity adjustment value and start phase adjustment value.

6. The magnetic resonance imaging apparatus according to claim 1, wherein the multi-dimensional spatial selective excitation pulses further includes a sub-two-dimensional selective excitation pulse to be applied together with the two-dimensional selective excitation pulse, and
the adjustment unit includes a sub-pulse adjustment unit determining an application strength and an irradiation frequency of the said sub-two-dimensional selective excitation pulse so that a main lobe by the sub-two-dimensional selective excitation pulse cancels out a side lobe by the two-dimensional selective excitation pulse.

7. The magnetic resonance imaging apparatus according to claim 6,
wherein a start phase of the sub-two-dimensional selective excitation pulse is different by 180 degrees from a start phase of the two-dimensional selective excitation pulse.

8. The magnetic resonance imaging apparatus according to claim 6,
wherein the oscillation number of the oscillating gradient magnetic field pulse is smaller than that of the oscillating gradient magnetic field pulse of the multi-dimensional spatial selective excitation pulses that obtain the same main lobe and does not include the sub-two-dimensional selective excitation pulse.

9. The magnetic resonance imaging apparatus according to claim 2,
wherein the control unit is provided with a reception unit accepting the imaging parameter input from a user and a sequence determination unit determining a three-dimensional selective excitation sequence optimal for the accepted imaging parameter from a plurality of the three-dimensional selective excitation sequences in which application patterns of the multi-dimensional spatial selective excitation pulses are different based on the accepted imaging parameter.

10. The magnetic resonance imaging apparatus according to claim 2,
wherein the control unit is provided with a reception unit receiving the imaging parameter and a three-dimensional selective excitation sequence to be used for imaging as well as a change plan presentation unit analyzing the received imaging conditions and three-dimensional selective excitation sequence and creating and presenting the said imaging conditions or a change plan of the said three-dimensional selective excitation sequence, and
the three-dimensional selective excitation sequence to be used for imaging and the change plan are selected from among a plurality of the three-dimensional selective excitation sequences whose application patterns of the multi-dimensional spatial selective excitation pulses to be kept in advance are different.

11. The magnetic resonance imaging apparatus according to claim 3, wherein the excitation region display unit displays the excitation regions on a positioning image.

12. The magnetic resonance imaging apparatus according to claim 4,
wherein the excitation region adjustment unit adjusts the oscillation number of the oscillating gradient magnetic field pulses so that the number becomes larger as a relative distance between the main lobe and the side lobe becomes longer and adjusts an application number of the multi-dimensional spatial selective excitation pulses so that the number becomes larger as a relative distance between the side lobes becomes longer.

13. The magnetic resonance imaging apparatus according to claim 5,
wherein the intensity adjustment value is calculated as a ratio of a half-value width of the excitation profile of the main lobe and a width in the same direction of a target excitation region, and
the start phase adjustment value is calculated as a ratio of a distance between a center of the excitation profile of the main lobe and a magnetic field center and a distance between the center of the excitation profile of the main lobe and the center of the excitation profile of the side lobe.

14. A magnetic resonance imaging method using a three-dimensional spatial selective excitation sequence that applies a plurality of multi-dimensional spatial selective excitation pulses comprised of a two-dimensional selective excitation pulse and an oscillating gradient magnetic field pulse, including:
   a sequence determination step of determining a three-dimensional spatial selective excitation sequence to be used for imaging from among a plurality of the three-dimensional spatial selective excitation sequences in which application patterns of the multi-dimensional spatial selective excitation pulses are different,
   an adjustment step of adjusting the multi-dimensional spatial selective excitation pulses of the determined three-dimensional spatial selective excitation sequence so as to selectively excite a target region, and
   a main imaging step of executing main imaging by the selected three-dimensional spatial selective excitation sequence using the adjusted multi-dimensional spatial selective excitation pulse,
   wherein the sequence determination step has a display step of displaying an excitation step by the said selected three-dimensional spatial selective excitation sequence each time the selection is accepted.

15. A magnetic resonance imaging method using a two-dimensional selective excitation pulse that applies a selective excitation pulse comprised of a two-dimensional selective excitation pulse and an oscillating gradient magnetic field pulse, wherein the selective excitation pulse includes a sub-two-dimensional selective excitation pulse to be applied together with the two-dimensional selective excitation pulse, and the said method including:
   a sub-pulse adjustment step of adjusting an application strength and an irradiation frequency of the sub-two-dimensional selective excitation pulse so that a main lobe by the sub-two-dimensional selective excitation pulse cancels out a side lobe by the two-dimensional selective excitation pulse, and
   a main imaging step of executing main imaging by a two-dimensional selective excitation sequence using the adjusted sub-two-dimensional selective excitation pulse.

* * * * *